United States Patent
Berthoud et al.

(10) Patent No.: US 9,624,324 B2
(45) Date of Patent: Apr. 18, 2017

(54) METAL COMPLEX WITH A BRIDGED CYCLOPENTADIENYL AMIDINE LIGAND

(71) Applicant: LANXESS Elastomers B.V., Geleen (NL)

(72) Inventors: Alexandra Berthoud, Neerharen (BE); Victor Quiroga Norambuena, Lanaken (BE); Gerhard Van Doremaele, Sittard (NL); Martin Alexander Zuideveld, Kelmis (BE); Philip Mountford, Oxford (GB); Richard Thomas William Scott, Maastricht (NL)

(73) Assignee: ARLANXEO Netherlands B.V., Geleen (NL)

( * ) Notice: Subject to any disclaimer, the term of this patent is extended or adjusted under 35 U.S.C. 154(b) by 0 days.

(21) Appl. No.: 14/889,242

(22) PCT Filed: May 7, 2014

(86) PCT No.: PCT/EP2014/059377
§ 371 (c)(1),
(2) Date: Nov. 5, 2015

(87) PCT Pub. No.: WO2014/180922
PCT Pub. Date: Nov. 13, 2014

(65) Prior Publication Data
US 2016/0122455 A1    May 5, 2016

(30) Foreign Application Priority Data
May 8, 2013 (EP) .................................... 13167137

(51) Int. Cl.
*C08F 4/64*   (2006.01)
*C08F 4/76*   (2006.01)
(Continued)

(52) U.S. Cl.
CPC .......... *C08F 210/18* (2013.01); *C07C 249/02* (2013.01); *C07C 251/24* (2013.01);
(Continued)

(58) Field of Classification Search
CPC .......... C08F 4/6592; C08F 4/76; C07F 17/00; C07F 7/28; B01J 31/38
See application file for complete search history.

(56) References Cited

U.S. PATENT DOCUMENTS 7,732,643 B2 *  6/2010  Hanaoka ................. C07C 33/34
                                                    568/308
7,776,980 B2    8/2010  Mihan et al.
(Continued)

FOREIGN PATENT DOCUMENTS

CN       102070732 A  *  5/2011  .............. C08F 10/10
WO    WO 2011/076775 A1  *  6/2011  ............ C08F 210/18

OTHER PUBLICATIONS

Guo, D.; Tong, H.-B.; Zhou, M. Acta Cryst. 2009, E65, m611.*
(Continued)

*Primary Examiner* — Rip A Lee

(57) ABSTRACT

The present invention relates to a new metal complex of the formula (1)
(Continued)

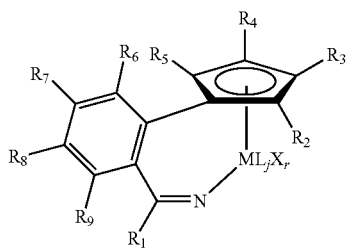

(1)

wherein:

M is a group 4-6 metal $R^1$ means is a substituent comprising a heteroatom of group 15, through which $R^1$ is bonded to the imine carbon atom;

$R^2$-$R^5$ are the same or different and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^2$-$R^5$ may be linked to each other to form a ring;

$R^6$-$R^9$ are the same or different and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^6$-$R^9$ may be linked to each other to form a ring;

L is an optional neutral Lewis basic ligand, and j is an integer denoting the number of neutral ligands L; and X Is an anionic ligand, and r is an integer denoting the number of anionic ligands X.

18 Claims, 6 Drawing Sheets

(51) Int. Cl.
| | | |
|---|---|---|
| C08F 210/18 | (2006.01) | |
| C07F 7/00 | (2006.01) | |
| C07C 257/18 | (2006.01) | |
| C07C 249/02 | (2006.01) | |
| C07C 251/24 | (2006.01) | |
| C07F 7/28 | (2006.01) | |
| C08F 4/6592 | (2006.01) | |

(52) U.S. Cl.
CPC ............ *C07C 257/18* (2013.01); *C07F 7/006* (2013.01); *C07F 7/28* (2013.01); *C07C 2101/10* (2013.01); *C08F 4/6592* (2013.01)

(56) References Cited

U.S. PATENT DOCUMENTS

| | | | | |
|---|---|---|---|---|
| 7,956,140 B2* | 6/2011 | Ijpeij | ....................... | C08F 10/00 526/160 |
| 8,084,385 B1* | 12/2011 | Nagy | ....................... | C08F 10/00 502/103 |
| 8,957,170 B2* | 2/2015 | Van Doremaele | .... | C08F 210/18 502/103 |

OTHER PUBLICATIONS

Chen, E.Y-X, et al., "Cocatalysts for Metal-Catalyzed Olefin Polymerization: Activators, Acrtivation Processes, and Structure-Activity Relationships", Chem Rev. 2000, 100, American Chemical Society, Washington DC. USA, pp. 1391-1434.

Guo, D., et al., "The ansa-bridged cyclopentadienyl titanium complex", Acta Cryst. (2009), E65, m611, available online at htpp//www.crossref.org/crossmark, 7 pages.

International Search Report from international application No. PCT/EP2014/059377, Oct. 8, 2014, 2 pages.

* cited by examiner

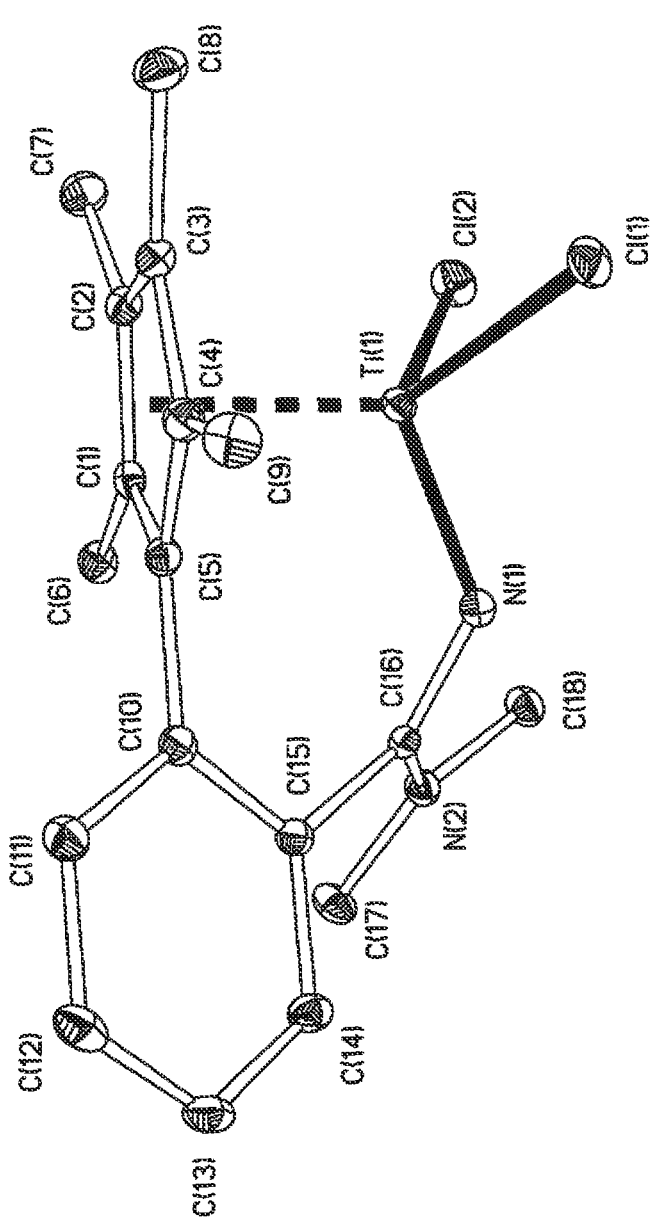
Figure 1 – X-ray picture of compound 2

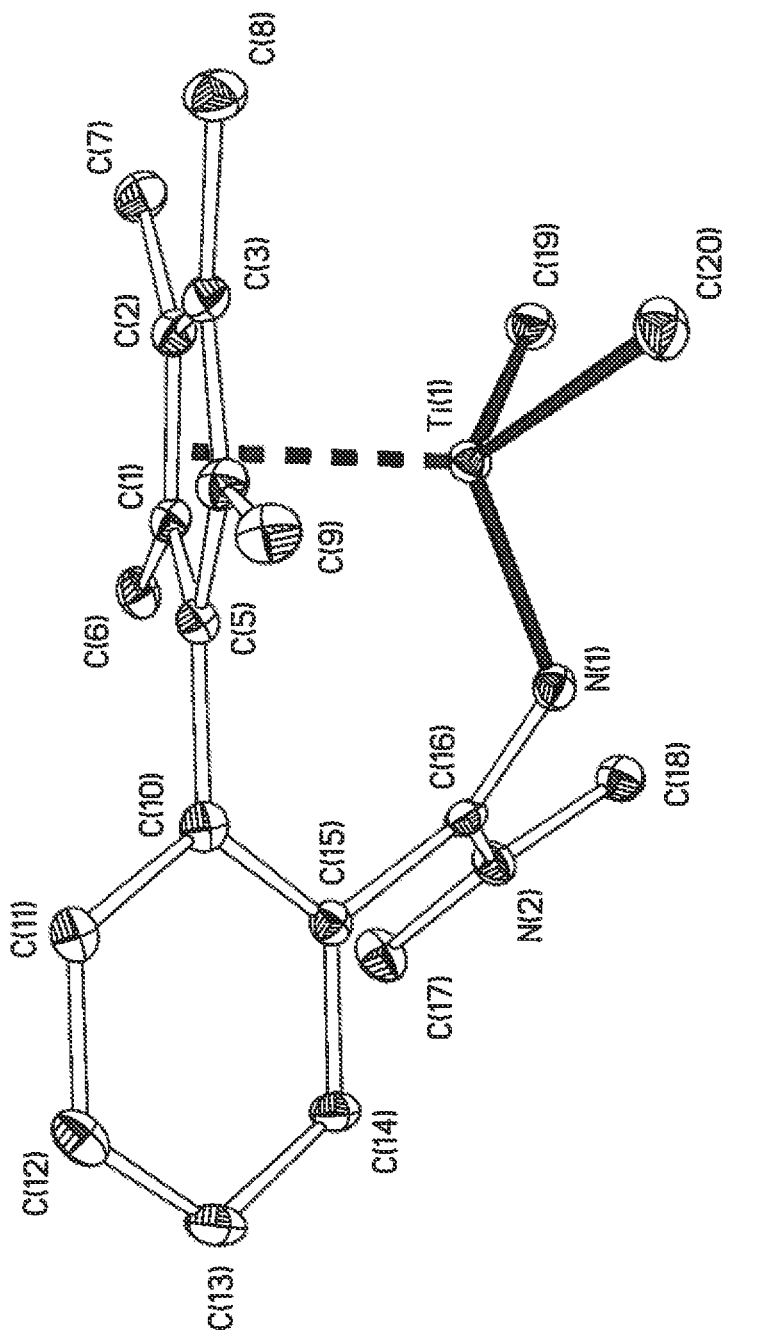
Figure 2 – X-ray picture of compound 3

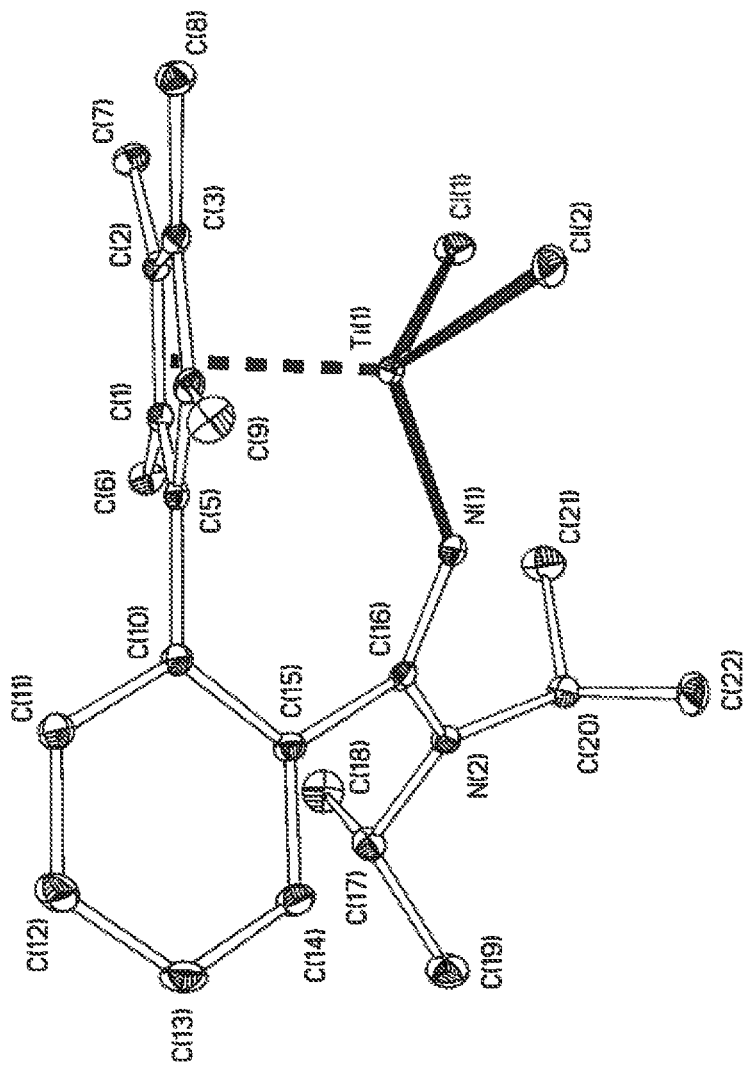
Figure 3 – X-ray picture of compound 5

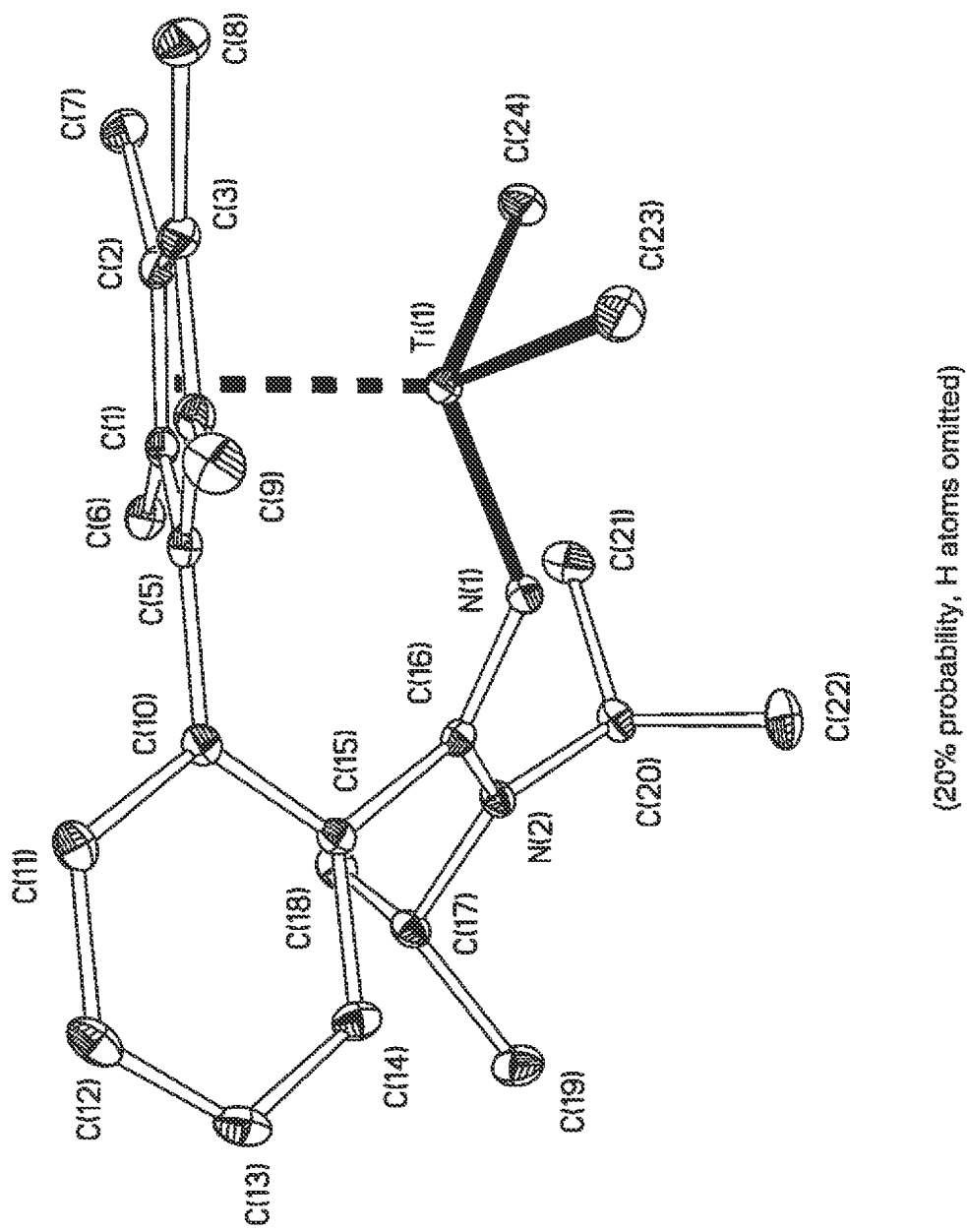
Figure 4 – X-ray picture of compound 6

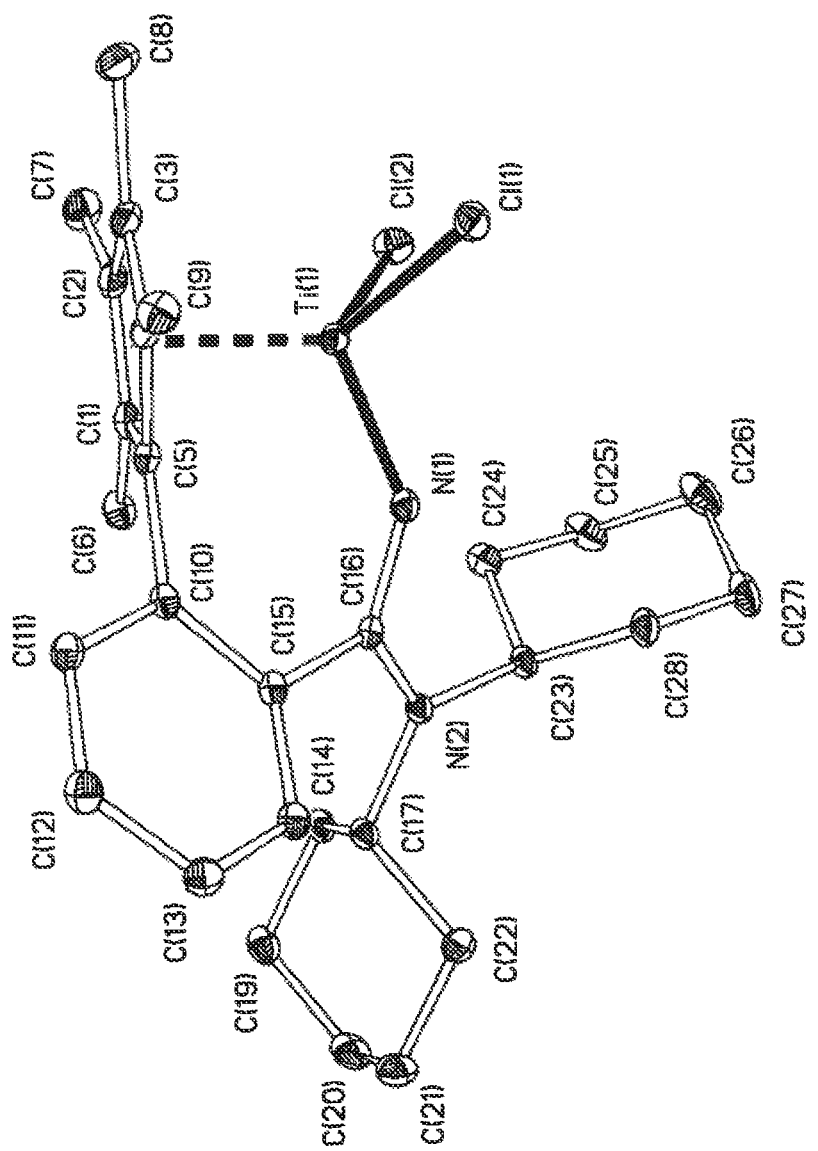
Figure 5 – X-ray picture of compound 8

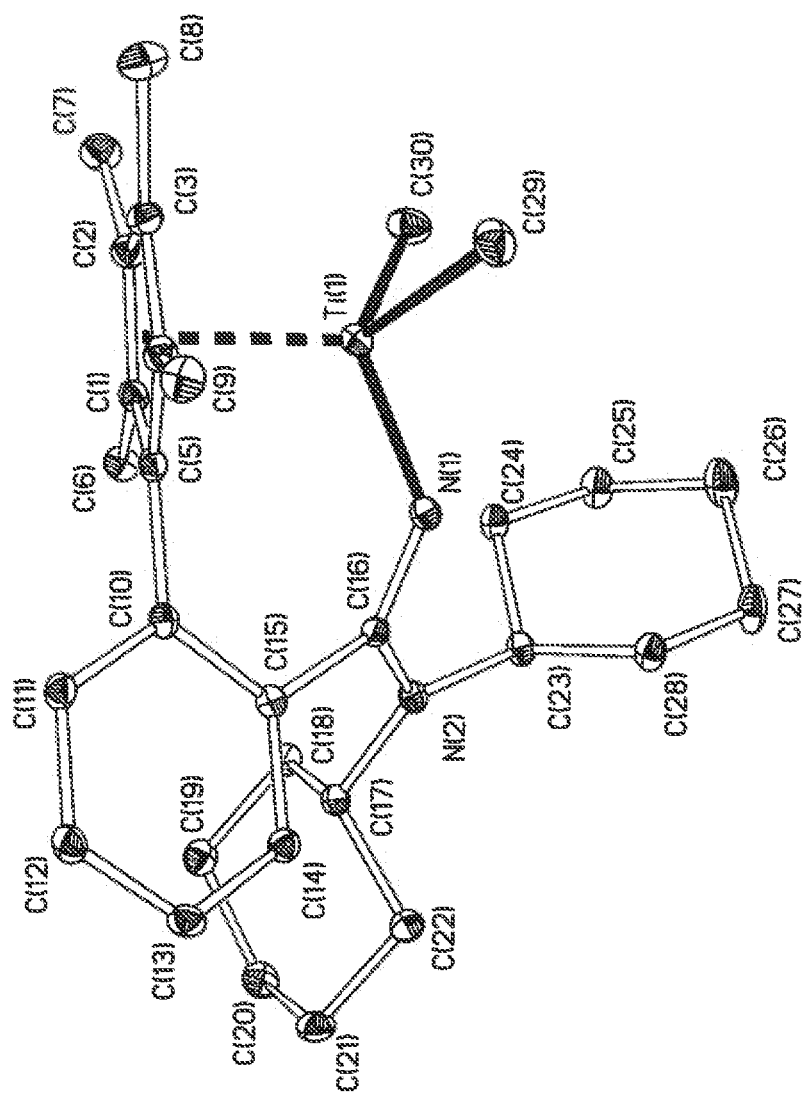
Figure 6 – X-ray picture of compound 9

METAL COMPLEX WITH A BRIDGED CYCLOPENTADIENYL AMIDINE LIGAND

The present invention relates to a metal complex containing a bridged cyclopentadienyl amidine ligand, a process for its preparation, a precursor, a catalyst system containing said metal complex and a process for manufacturing polymers wherein said metal complex or catalyst system is used.

A process for the polymerization of at least one olefin having 2 to 8 carbon atoms in the presence of a polymerization catalyst component comprising an amidine ligand, an activator, and optionally a scavenger is known from WO2005090418. WO2005090418 discloses a process for the copolymerization of ethylene and at least one additional alpha olefin having from 3 to 8 carbon atoms. Characterized in that said process is a catalyst system for olefin polymerization comprising an organometallic complex of a group 4 metal comprising an amidine ligand; and an activator. WO2005090418 discloses also a process for the copolymerisation of ethylene, alpha olefin and one or more non conjugated dienes. This process has a moderate ability to copolymerize non-conjugated dienes.

Catalyst components for the copolymerization of olefins having a bridged tetramethylcyclopentadienyl amido ligand are very well known in the art and well documented as part of the family of so-called "constrained geometry catalysts". Such components can display different polymerisation behaviours compared to closely related non-bridged catalysts.

It has been observed in EP1426379B1 that a catalyst comprising a ligand in which a cyclopentadienyl-type ligand is tethered to a ketimide-type ligand via an aryl linker can be employed for ethylene homopolymerisation and copolymerisations such ethylene-1-hexene copolymerisation. However, the disadvantage of such bridged cyclopentadienyl-ketimide catalysts is their limited capability to produce high molecular weight copolymers (see comparative examples).

A non-aromatic bridged cyclopentadienyl-amidinate titanium complex is known from D. Guo et al. Acta Cryst (2009), E65, m611. The combination of the short methylene bridge and small methyl amidinate ligand substituents suggest that this compound is of limited use as a polymerisation catalyst; the nature of the preparation also serves to preclude modifications such as introduction of larger ligand substituents which may result in Improved catalyst performance. Other complexes with a cyclopentadienyl ligand linked to another donor moiety via a non-aromatic bridge are mentioned in WO2006/100004; the metal employed in this instance is chromium.

A purpose of the invention is to provide a new class of catalyst components comprising bridged cyclopentadienyl amidine-type ligands that provide significantly higher diene affinity than the catalyst components in the known process embodied in WO2005090418 whilst providing higher molecular weight polymer than the aryl-bridged cyclopentadienyl-ketimide catalyst components described in EP1426379B1.

The process according to the invention employs the monomeric units of ethylene, propylene, 5-ethylidene-2-norbornene and 5-vinyl-2-norbornene and shows a high relative copolymerization rate for 5-vinyl-2-norbornene and 5-ethylidene-2-norbornene compared to ethylene. This results in improved diene monomer utilization during the polymerization process whilst providing EPDM polymers with increased level of incorporated 5-ethylidene-2-norbornene and/or 5-vinyl-2-norbornene.

Due to the higher fraction of 5-ethylidene-2-norbornene and/or 5-vinyl-2-norbornene non conjugated diolefin that is polymerized with only one of the double bonds, the polymer comprises increased numbers of double bonds originating from the 5-ethylidene-2-norbornene and/or 5-vinyl-2-norbornene available for curing. It is known that the double bonds originating from the 5-ethylidene-2-norbornene give a high curing speed; especially if a sulfur based curing system is used. This also applies for dicyclopentadiene (DCPD).

For these reasons, it is very desirable to use the polymer made with the process of the present invention for the production in peroxide curing processes, preferably for the production of hoses, cable and wire covering, profiles and thermoplastic vulcanizates.

DETAILS OF THE INVENTION

This objective is achieved with a metal complex of the formula (1)

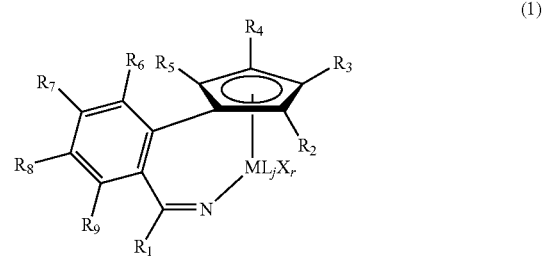

(1)

wherein:

M is a group 4-6 metal $R^1$ means is a substituent comprising a heteroatom of group 15, through which $R^1$ is bonded to the imine carbon atom;

$R^2$-$R^5$ are the same or different and each represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^2$-$R^5$ may be linked to each other to form a ring;

$R^6$-$R^9$ are the same or different and each represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with optionally substituted C1-20 hydrocarbon group(s), a C1-20 hydrocarbon-substituted amino group or the adjacent $R^8$-$R^9$ may be linked to each other to form a ring;

L is an optional neutral Lewis basic ligand, and j is an integer denoting the number of neutral ligands L; and X is an anionic ligand, and r is an integer denoting the number of anionic ligands X.

M

In a preferred embodiment the metal M of group 4 is titanium (Ti), zirconium (Zr) or hafnium (Hf), most preferably titanium (Ti), most preferably Ti is in the +4 oxidation state.

$R^1$

In a preferred embodiment of the present invention relates to a metal complex of the formula (1) wherein $R^1$ is of the general formula $-NR^{10}R^{11}$ with $R^{10}$ and $R^{11}$ being individually selected from the group of aliphatic C1-10 hydrocarbyl, halogenated aliphatic C1-10 hydrocarbyl, aromatic C6-20 hydrocarbyl and halogenated C6-20 aromatic hydrocarbonyl residues. $R^{10}$ optionally forming a heterocyclic structure with $R^{11}$ or with either one of the radicals $R^6$ to $R^9$ in particular with $R^9$. Preferred examples for $R^1$ are dimethylamide, diisopropylamide, dicyclohexylamide and N-dimethylphenyl N-ethylamide.

Substituents

Specific examples of the optionally substituted C1-10 alkyl group for the substituents $R^2$ to $R^9$ and the radical X include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group and a n-decyl group. Furthermore, the above substituents which are substituted with halogen atom(s) (especially fluorine atom(s)) are exemplified, and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, and the like. Among these, a methyl group, an ethyl group, an isopropyl group, a tert-butyl group, an amyl group and the like are preferred.

The optionally substituted C6-20 aryl group for $R^2$ to $R^9$ and the radical X include a phenyl group, a naphthyl group, an anthracenyl group and the like, and specific examples thereof Include, for example, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, a isopropylphenyl group, a n-butylphenyl group, a sec-butylphenyl group, a tertbutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, and an anthracenyl group. Furthermore, the above substituents which are substituted, for example, with halogen atom(s), more specifically with fluorine atom(s), are exemplified. As preferable aryl group, a phenyl group is exemplified.

The optionally substituted C7-20 aralkyl group of $R^2$ to $R^9$ and the radical X include a benzyl group, a naphthylmethyl group, an anthracenylmethyl group, a diphenylmethyl group and the like, and specific examples thereof include, for example, a benzyl group, a (2-methylphenyl)methyl group, a (3-methylphenyl)methyl group, a (4-methylphenyl) methyl group, a (2,3-dimethylphenyl)methyl group, a (2,4-dimethylphenyl)methyl group, a (2,5-dimethylphenyl) methyl group, a (2,6-dimethylphenyl)methyl group, a (3,4-dimethylphenyl)methyl group, a (2,3,4-trimethylphenyl) methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl) methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl) methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl)methyl group, a naphthylmethyl group, an anthracenylmethyl group, a diphenylmethyl group, and the above substituents substituted by halogen, more specifically, a fluorine-substituted aralkyl group. A benzyl group is exemplified as a preferable substituent.

Specific examples of the optionally substituted C1-10 alkoxy group for the substituents $R^2$ to $R^9$ and the radical X include a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, and a n-decyloxy group. Furthermore, the alkoxy groups substituted with halogen(s) are exemplified, and more specifically, a fluorine atom-substituted alkoxy group, in which the alkoxy group is substituted with fluorine atom(s), is exemplified. Preferably, a methoxy group, an ethoxy group, and a tert-butoxy group are exemplified.

The optionally substituted C6-20 aryloxy group for the substituents $R^2$ to $R^9$ and the radical X includes a phenoxy group, a naphthoxy group, and an anthracenoxy group. Furthermore, specific examples thereof include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethyl-phenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexyl-phenoxy group, a n-octylphenoxy group, a n-decylphenoxy group, a n-tetradecyl-phenoxy group, a naphthoxy group, an anthracenoxy group, and the above substituents substituted with halogen atom(s), and more specifically, a fluorine-substituted aryloxy group is exemplified.

The optionally substituted C7-20 aralkyloxy group for the substituents $R^2$ to $R^9$ and the radical X include a benzyloxy group, a naphthylmethoxy group, an anthracenylmethoxy group, and a diphenylmethoxy group. Furthermore, specific examples thereof include, for example, a benzyloxy group, a (2-methylphenyl)methoxy group, a (3-methyl-phenyl) methoxy group, a (4-methylphenyl)methoxy group, a (2,3-dimethylphenyl)-methoxy group, a (2,4-dimethylphenyl) methoxy group, a (2,5-dimethylphenyl)methoxy group, a (2,6-dimethylphenyl)methoxy group, a (3,4-dimethylphenyl)methoxy group, a (2,3,4-trimethylphenyl)methoxy group, a (2,3,5-trimethylphenyl)methoxy group, a (2,3,6-trimethylphenyl)methoxy group, a (3,4,5-trimethylphenyl) methoxy group, a (2,4,6-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)-methoxy group, a (sec-butylphenyl)methoxy group, a (tert-butylphenyl)methoxy group, a (n-pentylphenyl)methoxy group, a (neopentylphenyl)methoxy group, a (n-hexyl-phenyl)methoxy group, a (n-octylphenyl)methoxy group, a (n-decylphenyl)methoxy group, a (n-dodecylphenyl)methoxy group, a naphthylmethoxy group, an anthracenyl-methoxy group, a diphenylmethoxy group and the above substituents substituted with halogen(s), and more specifically, a fluorine atom-substituted aralkyloxy group is exemplified. A benzyloxy group is exemplified as a preferable substituent.

The C1-20 hydrocarbon-substituted silyl group for the substituents $R^1$ to $R^9$ and the radical X is a silyl group substituted with C1-20 hydrocarbon group(s). The hydrocarbon group as used herein includes, for example, C1-10 alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and C6-20 aryl groups such as a phenyl group, a tolyl group, a xylyl group, a naphthyl group, an anthracenyl group and the like. Such C1-20 hydrocarbon-substituted silyl group includes, for example, mono-substituted silyl groups such as a methylsilyl group, an ethylsilyl group, a phenylsilyl group and the like, di-substituted silyl groups such as a dimethylsilyl group, a diethylsilyl group, a diphenylsilyl group and the like, tri-substituted silyl groups such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethylsilyl group, a tri-n-pentylsilyl group, a tri-n-hexylsilyl group, a tricyclohexylsilyl group, a triphenylsilyl group and the like, preferably a trimethylsilyl group, a tert-butyldimethylsilyl group, and a triphenylsilyl group. Furthermore, the above substituted silyl groups in which the hydrocarbon groups are substituted with halogen atom(s), e.g., fluorine atom(s), are exemplified.

The C1-20 hydrocarbon-substituted amino group for the substituents $R^2$ to $R^9$ and the radical X preferably is an amino group substituted with two hydrocarbon groups. The hydrocarbon group as used herein includes, for example, C1-10 alkyl groups such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-decyl group and the like, and C6-20 aryl groups such as a phenyl group, a tolyl group, a xylyl group, a naphthyl group, an anthracenyl group and the like. Such C1-20 hydrocarbon-substituted amino group includes, for example, a dimethylamino group, a diethylamino group, a di-n-propylamino group, a diisopropylamino group, a di-n-butylamino group, a di-sec-butylamino group, a di-tert-butylamino group, a di-Isobutylamino group, a tert-butylisopropylamino group, a di-n-hexylamino group, a di-n-octylamino group, a di-n-decylamino group, a diphenylamino group and the like, preferably, a dimethylamino group and a diethylamino group.

The halogen atom for the substituents $R^2$ to $R^9$ and the radical X include a fluorine atom, a chlorine atom, a bromine atom and an iodine atom, preferably a fluorine atom and a chlorine atom.

$R^2$-$R^5$

In a preferred embodiment $R^2$-$R^5$ are the same or different and each represents a hydrogen atom or a C1-5 alkyl group, in particular each represents methyl.

$R^6$-$R^9$

In a preferred embodiment $R^6$-$R^9$ are the same or different and each represents a hydrogen atom.

X

In a preferred embodiment X means a halogen atom, a C1-10 alkyl group, a C7-20 aralkyl group, a C6-20 aryl group or a C1-20 hydrocarbon-substituted amino group, and more preferably, a halogen atom and a C1-10 hydrocarbon-substituted amino group, most preferably Cl, F, Br, methyl, benzyl, methyltrimethylsilyl, phenyl, methoxyphenyl, dimethoxyphenyl, N,N-dimethylaminophenyl, bis(N,N-dimethylamino)phenyl, fluorophenyl, difluorophenyl, trifluorophenyl, tetrafluorophenyl, perfluorophenyl, trialkylsilylphenyl, bis(trialkylsilyl)phenyl and tris(trialkylsilyl)phenyl. Most preferred are Cl or methyl. In case of more than one X the given meanings are independently.

r

The number of anionic ligands X is denoted as r and depends on the valency of the metal and the valency of the anionic ligand. Whereas the valency of the Group 5 and 6 metals can be as high as 6+, the preferred catalyst metals are Group 4 metals in their highest oxidation state (i.e. 4+) and the preferred anionic ligands X are monoanionic (such as a halogen or a hydrocarbyl group—especially methyl and benzyl). Thus, the preferred catalyst component contains a bridged cyclopentadienyl amidine ligand and two $R^1$, for instance chloride (or methyl) ligands bonded to the Group 4 metal. In contrast, the highest oxidation state of Group 5 and 6 metals are 5+ and 6+ respectively and will require a higher number or a more highly charged anionic ligand to satisfy overall charge neutrality. In some instances, the metal of the catalyst component may not be in the highest oxidation state. For example, a titanium (III) component would contain only one anionic ligand and a titanium (IV) component would contain 2 anionic ligands X.

L

Preferred is a metal complex of the formula (1) wherein L is an ether, a thioether, a amine, a tertiary phosphane, an imine, a nitrile, an isonitrile, or a bi- or oligodentate donor.

If more than one ligand L is present they may have different meanings.

The number "j" of neutral ligands in the metal complex of formula (1) may range from 0 to the amount that satisfies the 18-electron rule, as known in the art. Preferably from 0 to 2. In the preferred embodiment the number of neutral ligands L is 0.

Suitable ethers are diethyl ether, dipropyl ether, diisopropyl ether, dibutyl ether, dihexyl ether, anisole, phenetole, butyl phenyl ether, methoxytoluene, benzyl ethyl ether, diphenyl ether, dibenzyl ether, veratrole, 2-epoxypropane, dioxane, trioxane, furan, 2,5-dimethylfuran, tetrahydrofuran, tetrahydropyrane, 1,2-diethoxyethane, 1,2-dibutoxyethane, and crown ethers. Suitable thioethers are dimethyl sulfide, diethyl sulfide, thiophene, and tetrahydrothiophene. Suitable amines such as methylamine, dimethylamine, trimethylamine, ethylamine, diethylamine, triethylamine, propylamine, diisopropylamine, butylamine, isobutylamine, dibutylamine, tributylamine, pentylamine, dipentylamine, tripentylamine, 2-ethylhexylamine, allylamine, aniline, N-methylaniline, N,N-dimethylaniline, N,N-diethylaniline, toluidine, cyclohexylamine, dicyclohexylamine, pyrrole, piperidine, pyridine, picoline, 2,4-lutidine, 2,6-lutidine, 2,6-di(t-butyl)pyridine, quinoline, and isoquinoline, preferably tertiary amines such as trialkylamines, pyridine, bipyridine, tetramethylethylenediamine (TMEDA), and (−)-sparteine). Suitable tertiary phosphanes are triphenylphosphine and trialkylphosphines. Suitable of imines are ketimines, guanidines, iminoimidazolidines, phosphinimines and amidines. Suitable bidentate ligands are diimines, alkyl or aryldiphoshanes, dimethoxyethane. Suitable oligodentate ligands are triimines (such as tris(pyrazolyl)alkanes), cyclic multidentate ligands comprising heteroatoms of group 13-17, including crown ethers optionally having heteroatoms of group 13-17, azo-crown ethers optionally having heteroatoms of group 13-17, phospha-crown ethers optionally having heteroatoms of group 13-17, crown ethers having combinations of heteroatoms of group 15-16 optionally having heteroatoms of group 13-17 and crown ethers containing heteroatoms of group 14-17 or combinations thereof.

Suitable nitriles are those of the formula, $R^1C\equiv N$, where $R^1$ is individually selected from the group of aliphatic hydrocarbyl, halogenated aliphatic hydrocarbyl, aromatic hydrocarbyl and halogenated aromatic hydrocarbonyl residues. Preferred nitriles are acetonitrile, acrylonitrile, cyclohexanedinitrile, benzonitrile, pentafluorobenzonitrile, 2,6-difluorobenzonitrile, 2,6-dichlorobenzonitrile, 2,6-dibromobenzotrile, 4-fluoro-2-trifluoromethyl benzonitrile, 3-pyridinecarbonitrile.

Suitable isonitriles are those of the formula, $R^1C\equiv N$, where $R^1$ is individually selected from the group of aliphatic hydrocarbyl, halogenated aliphatic hydrocarbyl, aromatic hydrocarbyl and halogenated aromatic hydrocarbonyl residues. A preferred isonitriles is tert-butyl isocyanide ($^t$BuNC), ethyl isocyanoacetate, p-toluenesulfonylmethyl isocyanide and cyclohexyl isocyanide preferably tert-butyl isonitrile ($^t$BuNC).

A preferred neutral Lewis basic ligand L means t-Butyl-isonitrile ($^t$BuNC).

Process

The invention further relates to a process for the manufacturing of a metal complex according to the present invention which comprises reacting the substituted cyclopentadiene compound of the formula (2)

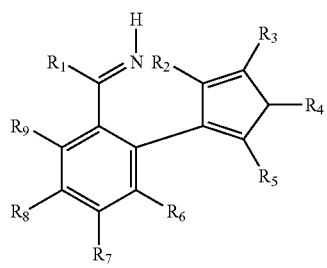

(2)

wherein $R^1$-$R^9$ have the same meaning as given above, with a metal compound represented by the formula (3)

$$MX_{(r+2)}L_j \quad (3),$$

wherein M, X, L and r and j have also the same meaning as given above, which also applies for the preferred meaning of those radicals.

The meaning of X for the transition metal compound of the formula (3) is already explained. Said transition metal compound in which X is a C1-5 hydrocarbon-substituted amino group and/or a halogen atom is preferably used for the production of the metal complex.

The transition metal compound represented by the formula (3) includes tetrakis-(dimethylamino)titanium, tetrakis(diethylamino)titanium, tetrakis(dimethylamino)-zirconium, tetrakis(diethylamino)zirconium, tetrakis(dimethylamino)hafnium, tetrakis(diethylamino)hafnium, tris(dimethylamino)titanium chloride, tris(diethyl-amino)titanium chloride, tris(dimethylamino)zirconium chloride, tris(diethylamino)-zirconium chloride, tris(dimethylamino)hafnium chloride, tris(diethylamino)hafnium chloride, bis(dimethylamino)titanium dichloride, bis(diethylamino) titanium dichloride, bis(dimethylamino)zirconium dichloride, bis(diethylamino)zirconium dichloride, bis(dimethylamino)hafnium dichloride, and bis(diethylamino)hafnium dichloride.

The above reaction is usually carried out in an inert solvent to the reaction. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like, preferably aromatic hydrocarbon solvents such as benzene, toluene and the like; aliphatic hydrocarbon solvents such as hexane, heptane and the like. One or a mixture of two or more of the solvents is used. The amount of a solvent to be used is usually in the range of 1 to 200 parts by weight, preferably 3 to 50 parts by weight relative to 1 part by weight of the substituted cyclopentadiene ligand compound represented by the formula (2).

This reaction can be usually carried out by adding the substituted cyclopentadiene represented by the formula (2) to a solvent and then adding the transition metal compound represented by the formula (3) thereto. Thus the transition metal complex represented by the formula (1) can be obtained.

The reaction temperature is usually in the range of −100° C. to the boiling point of the solvent, preferably −80 to 120° C.

The transition metal complex wherein two X are each a substituted amino group can be converted to a halide thereof by reacting with a halogen compound such as a chlorosilane compound or a hydrogen chloride. The transition complex wherein two X are each a halide may be converted to an alkyl thereof by reacting the dihalide complex with an alkyl lithium or alkyl magnesium compound.

Precursor

The invention further relates to a compound of the above given formula (2).

Although the double bounds in the cyclopentadienyl ring are localized in the generic formula (2), it shall also encompass the three double bond isomers (2a), (2b) and (2c)

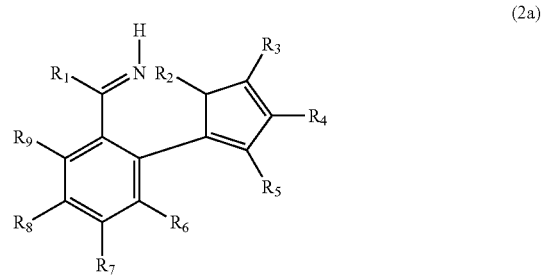

(2a)

(2b)

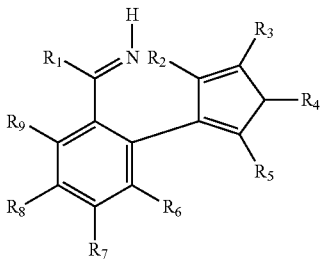

(2c)

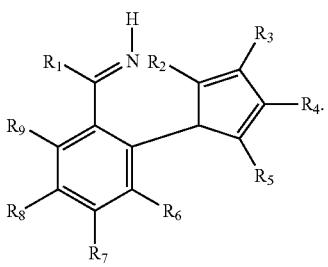

Process for Precursor

The invention further relates to a process for the manufacturing of a compound of the formula (2) wherein the nitrile of formula (4) or the oxime of formula (5)

(4)

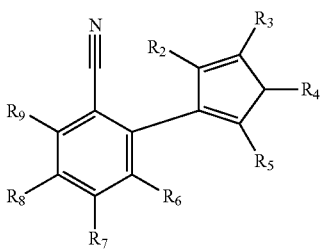

(5)

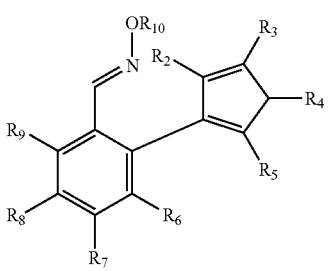

is reacted with an organic lithium compound $LiR^1$ or an organic magnesium compound $Mg(Hal)R^1$
wherein $R^1$-$R^9$ have the same meaning as given above,
$R^{10}$ represents a hydrogen atom, an optionally substituted C1-10 alkyl group, an optionally substituted C6-20 aryl group, an optionally substituted C7-20 aralkyl group or a silyl group optionally substituted with optionally substituted C1-20 hydrocarbon(s) wherein those radicals may have the more preferred meaning as given above, in particular $R^{10}$ represents hydrogen or methyl and
Hal means a halide, preferably Cl, Br, I or F, in particular Br.

Preferably for $R^1$=$NMe_2$ the lithium compound $LiR^1$ and for $R^1$=$N(iPr)_2$ or $N(Cyclohexyl)_2$ the magnesium compound $Mg(Hal)R^1$ is used.

The reaction of the organic lithium compound $LiR^1$ or the organic magnesium compound as nucleophilic agent and the nitril of the formula (4) or the oxime of the formula (5) is usually carried out in an inert solvent to the reaction. Such a solvent includes, for example, aprotic solvents such as aromatic hydrocarbon solvents such as benzene, toluene and the like; aliphatic hydrocarbon solvents such as hexane, heptane and the like; ether solvents such as diethyl ether, tetrahydrofuran, 1,4-dioxane and the like; amide solvents such as hexamethylphosphoric amide, dimethylformamide and the like; polar solvents such as acetonitrile, propionitrile, acetone, diethyl ketone, methyl isobutyl ketone, cyclohexanone and the like; halogenated solvents such as dichloromethane, dichloroethane, chlorobenzene, dichlorobenzene and the like. One or a mixture of two or more of the solvents is used. The amount of a solvent to be used is usually in the range of 1 to 200 times, preferably 3 to 50 times the weight of the substituted cyclopentadiene of the formula (4) or (5).

The reaction temperature is usually in the range of −100° C. to the boiling point of a solvent, preferably −80 to 120° C.

After the reaction, if needed, water is added to the resulting reaction mixture. The mixture is then separated into an organic layer and an aqueous layer to give a solution of the objective compound as the organic layer. When the organic layer and the aqueous layer cannot be easily separated due to use of a solvent compatible with water or use of a small amount of solvent in said reaction, the separation may be carried out after addition of a water-insoluble organic solvent such as toluene, ethyl acetate, chlorobenzene and the like to the reaction mixture. The imine compound represented by the formula (2) can be purified, for example, by washing said solution of the compound with water, drying said solution, and then distilling off the solvent, and further by methods such as recrystallization, distillation, column chromatography treatment and the like.

The invention also relates to a supported catalyst which comprises an organometallic compound of formula (1), a supporting material and optionally a scavenger and/or an activator.

A supporting material is defined as an inorganic or organic compound that does not dissolve in the inert hydrocarbon solvent in which the process of the invention is carried out. Suitable inorganic supports include silica, magnesium halides, such as $MgF_2$, $MgCl_2$, $MgBr_2$, $MgI_2$, zeolites, and alumina. Suitable organic supports include polymers. Some non-limiting examples of polymeric supports are polyolefins such as polystryrene, polypropylene and polyethylene, polycondensates such as polyamides and polyesters and combinations thereof.

The invention further provides a catalyst system comprising
a) a metal complex of the formula (1) according to the present invention and
b) an activator and
c) optionally a scavenger.

The preferred metal complex of compound a) is mentioned above. A scavenger c) is a compound that reacts with impurities present in the process of the invention, which are poisonous to the catalyst.

In a preferred embodiment of the present invention the scavenger c) as of the catalyst system is a hydrocarbyl of a metal or metalloid of group 1-13 or its reaction products with at least one sterically hindered compound containing a group 15 or 16 atom.

Preferably, the group 15 or 16 atom of the sterically hindered compound bears a proton. Examples of these sterically hindered compounds are tert-butanol, iso-propanol, triphenylcarbinol, 2,6-di-tert-butylphenol, 4-methyl-2, 6-di-tert-butylphenol, 4-ethyl-2,6-di-tert-butylphenol, 2,6-di-tert-butylanin, 4-methyl-2,6-di-tert-butylaniln, 4-ethyl-2,6-di-tert-butylanilin, HMDS (hexamethyldisilazane), diisopropylamine, di-tert-butylamine, diphenylamine and the like. Some non-limiting examples of scavengers are butyllithium including its isomers, dihydrocarbylmagnesium, and hydrocarbylzinc and their reaction products with a sterically hindered compound or an acid, such as HF, HCl, HBr, HI. Furthermore organoaluminium compounds (E) as defined below can be used as activator b), in particular hydrocarbylaluminoxanes like methylaluminoxane (MAO).

Activators of the component b) for single-site catalysts are fairly well known in the art. These activators often comprise a group 13 atom, such as boron or aluminium. Examples of these activators are described in *Chem. Rev.*, 2000, 100, 1391 by E. Y-X. Chen and T. J. Marks. A preferred activator b) is a borane (C1), a borate (C2, C3) or an organoaluminum compound (E) like alkylaluminoxane such as methyl aluminoxane (MAO). The activator for activation preferably is any boron compound of the following (C1) to (C3) and/or an organoaluminum compound (E). The organoaluminum compound (E) may be employed as a scavenger and/or an activator.

(C1) A boron compound represented by the general formula $BQ_1Q_2Q_3$
(C2) A boron compound represented by the general formula $G(BQ_1Q_2Q_1Q_4)$
(C3) A boron compound represented by the general formula $(J-H)(BQ_1Q_2Q_3Q_4)$ $Q_1$ to $Q_3$ are a halogen atom, hydrocarbon group, halogenated hydrocarbon group, substituted silyl group, alkoxy group or di-substituted amino group, and they may be the same or different. $Q_1$ to $Q_3$ are preferably a halogen atom, hydrocarbon group having 1 to 20 carbon atoms, halogenated hydrocarbon group having 1 to 20 carbon atoms, substituted silyl group having 1 to 20 carbon atoms, alkoxy group having 1 to 20 carbon atoms or amino group having 2 to 20 carbon atoms, and more preferably, $Q_1$ to $Q_3$ are a halogen atom, hydrocarbon group having 1 to 20 carbon atoms, or halogenated hydrocarbon group having 1 to 20 carbon atoms. Further preferably, $Q_1$ to $Q_3$ are a fluorinated hydrocarbon group having 1 to 20 carbon atoms containing at least one fluorine atom, and particularly preferably, $Q_1$ to $Q_3$ are a fluorinated aryl group having 6 to 20 carbon atoms containing at least one fluorine atom. $Q_4$ has the same meaning as one of the radicals $Q_1$ to $Q_3$ and $Q_1$ to $Q_4$ may be the same or different. G is an inorganic or organic cation, J is a neutral Lewis base, and (J-H) is a Bronsted acid.

In the boron compound (C1) represented by the general formula $BQ_1Q_2Q_Q$, B is a boron atom in the trivalent valence state, $Q_1$ to $Q_3$ have the above mentioned meanings and may be the same or different.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenyl-bis(pentafluoro-phenyl)borane and the like, and tris(pentafluorophenyl)borane is most preferable.

In the boron compound (C2) represented by the general formula $G(BQ_1Q_2Q_3Q_4)$, $G^+$ is an inorganic or organic cation, B is a boron atom in the trivalent valence state, and $Q_1$ to $Q_4$ are as defined for $Q_1$ to $Q_3$ in the above-mentioned (C1).

Specific examples of the inorganic cation G in a compound represented by the general formula $G(BQ_1Q_2Q_3Q_4)$ include a ferrocenium cation, alkyl-substituted ferrocenium cation, sliver cation and the like, specific examples of the organic cation G thereof include a triphenylmethyl cation and the like. G is preferably a carbenium cation, and particularly preferably a triphenylmethyl cation.

Examples of $(BQ_1Q_2Q_3Q_4)$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluoro-phenyl)borate, tetrakis(3,5-bistrifluoromethylphenyl)borate and the like.

As specific combination of them, ferroceniumtetrakis(pentafluorophenyl)borate, 1,1'-dimethylferroceniumtetrakis(pentafluorophenyl)borate, silvertetrakis(pentafluorophenyl)borate, triphenylmethyltetrakis-(pentafluorophenyl)borate, triphenylmethyltetrakis(3,5-bistrifluoromethylphenyl)borate and the like are listed, and triphenylmethyltetrakis(pentafluorophenyl)borate is most preferable.

In the boron compound (C3) represented by the general formula $(J-H)^+(BQ_1Q_2Q_3Q_4)$, J is a neutral Lewis base, (J-H) is a Bronsted acid, B is a boron atom in the trivalent valence state, and $Q_1$ to $Q_4$ are as defined for $Q_1$ to $Q_4$ in the above-mentioned Lewis acid (C1).

Specific examples of the Bronsted acid $(J-H)^+$ In a compound represented by the general formula (J-H) $(BQ_1Q_2Q_3Q_4)$ include a trialkyl-substituted ammonium, N,N-dialkylanilinium, dialkylammonium, triaryl phosphonium and the like, and as the $(BQ_1Q_2Q_3Q_4)$, the same compounds as described above are listed. As specific combination of them, there are listed triethylammoniumtetrakis(pentafluoro-phenyl)-borate, tripropylammoniumtetrakis(pentafluorophenyl)borate, tri(n-butyl)ammonium-tetrakis(pentafluorophenyl)borate, tri(n-butyl)ammoniumtetrakis(3,5-bistrifluoromethyl-phenyl)borate, N,N-dimethylammoniumtetrakis(pentafluoro-phenyl)borate, N,N-diethylaniliniumtetrakis(penta-fluorophenyl)borate, N,N-2,4,6-pentamethylanilinium-tetrakis(pentafluorophenyl)borate, N,N-dimethylanilinium-tetrakis(3,5-bistrifluoromethyl-phenyl)borate, diisopropyl-ammoniumtetrakis(penta-fluorophenyl)borate, dicyclohexyl-ammoniumtetrakis-(pentafluorophenyl)borate, triphenylphosphoniumtetrakis(penta-fluorophenyl)borate, tri(methylphenyl)phosphoniumtetrakis(pentafluorophenyl)borate, tri(dimethylphenyl)-phosphonium-tetrakis (pentafluorophenyl)borate and the like, and tri(n-butyl) ammonium-tetrakis(pentafluorophenyl)borate or N,N-dimethylaniliniumtetrakis(pentafluoro-phenyl)borate is most preferable.

The molar ratio of metal complex:activating cocatalyst C1-C3 employed preferably ranges from 1:10 to 1:0, more preferably ranges from 1:5 to 1:0, and most preferably from 1:3 to 1:1.

The organoaluminum compound (E) is an aluminum compound having a carbon-aluminum bond, and one or more of aluminum compounds selected from the following (E1) to (E3) are preferable.

(E1) An organoaluminum compound represented by the general formula $T^1_aAlZ_{3-a}$
(E2) A cyclic aluminoxane having a structure represented by the general formula $\{-Al(T^2)-O-\}_b$
(E3) Linear aluminoxane having a structure represented by the general formula $T^3\{-Al(T^3)-O-\}_cAlT^3_2$
(wherein, each of $T^1$, $T^2$ and $T^3$ is hydrocarbon group, and all $T^1$, all $T^2$ and all $T^3$ may be the same or different respectively. Z represents a hydrogen atom or halogen atom, and all Z's may be the same or different. 'a' represents a number satisfying 0<a≤3, 'b' is an integer of 2 or more, and 'c' is an integer of 1 or more.).

The hydrocarbon group in E1, E2 or E3 is preferably a hydrocarbon group having 1 to 8 carbon atoms, and more preferably an alkyl group.

Specific examples of the organoaluminum compound (E1) represented by the general formula $T^1_a AlZ_{3-a}$ Include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth.

A preferred activator-scavenger combination is $[CPh_3][B(C_6F_5)_4]/MAO$.

Specific examples of cyclic aluminoxane E2 having a structure represented by the general formula $\{—Al(T^2)-O—\}_b$ and the linear aluminoxane E3 having a structure represented by the general formula $T^3\{-Al(T^3)-O—\}_c AlT^3_2$ include alkyl groups such as a methyl group, ethyl group, n-propyl group, isopropyl group, n-butyl group, isobutyl group, n-pentyl group, neopentyl group and the like. b is an integer of 2 or more, c is an integer of 1 or more. Preferably, $T^2$ and $T^3$ represent a methyl group or isobutyl group, and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which Ia trialkylaluminum (for example, trimethylaluminum and the like) is allowed to contact with a metal salt containing crystal water (for example, copper sulfate hydrate and the like) to produce aluminoxane.

The molar ratio of metal complex (1):scavenger c) employed preferably ranges from 0.1:1000 to 0.1:10, more preferably ranges from 0.1:1000 to 0.1:300, and most preferably from 0.14:600 to 0.14:400.

The invention further provides a process for the polymerization of a polymer by polymerizing at least one olefinic monomer comprising contacting said monomer with a metal complex of formula (1).

Polymerization

The preferred process for polymerization is generally concluded by consulting at least one olefinic monomer with the metal complex of the formula (1) or the catalyst system according to the present invention in the gas phase, in slurry, or in solution in an Inert solvent preferable a hydrocarbon solvent. Suitable solvents are in the gas phase, in slurry, or in solution in an inert solvent preferable a hydrocarbon solvent. Suitable solvents are a $C_{5-12}$ hydrocarbon such as pentane, hexane, heptane, octane, Isomers and mixtures thereof, cyclohexane, methylcyclohexane, pentamethyl heptane and hydrogenated naphtha. The process of the Invention may be conducted at temperatures from 10 to 250° C., depending on the product being made.

Monomer Definition

An olefinic monomer is understood to be a molecule containing at least one polymerizable double bond.

Suitable olefinic monomers are $C_{2-20}$ olefins. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, and $C_{4-12}$ straight chained or cyclic hydrocarbyl radicals which are unsubstituted or substituted by a $C_{1-4}$ alkyl radical. Illustrative non-limiting examples of such a-olefins are propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-hepta-decene, 1-octadecene, 1-nonadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 9-methyl-1-decene, 11-methyl-1-dodecene and 12-ethyl-1-tetradecene. These a-olefins may be used in combination.

The monomer may also be a polyene comprising at least two double bonds. The double bonds may be conjugated or non-conjugated in chains, ring systems or combinations thereof, and they may be endocyclic and/or exocyclic and may have different amounts and types of substituents. This means that the polyene may comprise at least one aliphatic, alicyclic or aromatic group, or combinations thereof.

Suitable polyenes include aliphatic polyenes and alicyclic polyenes. More specifically, aliphatic polyenes can be mentioned, such as 1,4-hexadiene, 3-methyl-1,4-hexadiene, 4-methyl-1,4-hexadiene, 5-methyl-1,4-hexadiene, 4-ethyl-1,4-hexadiene, 1,5-hexadiene, 3-methyl-1,5-hexadiene, 3,3-dimethyl-1,4-hexadiene, 5-methyl-1,4-heptadiene, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methyl-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 1,6-octadiene, 6-methyl-1,6-octadiene, 7-methyl-1,6-octadiene, 6-ethyl-1,6-octadiene, 6-propyl-1,6-octadiene, 6-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nonadiene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicylic polyenes may consist of at least one cyclic fragment. Examples of these alicyclic polyenes are vinylcyclohexene, vinylnorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclohexane, 1,4-diallylcyclohexane, 1-allyl-5-vinylcyclooctane, 1,5-diallylcyclooctane, 1-allyl-4-isopropenylcyclohexane, 1-isopropenyl-4-vinylcyclohexane and 1-isopropenyl-3-vinylcyclopentane, and 1,4-cyclohexadiene. Preferred polyenes are polyenes having at least one endocyclic double bond and optionally at least one exocyclic double bond, such as 5-methylene-2-norbornene and 5-ethylidene-2-norbornene, 5-vinylnorbornene, and 2,5-norbornadiene, dicyclopentadiene and vinylcyclohexene.

Examples of aromatic polyenes are divinylbenzene (including its isomers), trivinyl-benzene (including its isomers) and vinylisopropenylbenzene (including its isomers).

All of the above-mentioned monomers may be further substituted with at least one group comprising a heteroatom of group 13-17, or combinations thereof.

Homopolymers, copolymers and copolymers on the basis of 3 or more of the above-mentioned olefinic monomers and also blends thereof can be prepared with the process of the present invention.

In a preferred embodiment copolymers on the basis of ethylene, at least one $C_{3-12}$ alpha olefin, preferably propylene and at least one non-conjugated diene, preferably a diene selected from the group consisting of 5-methylene-2-norbornene 5-ethylidene-2-norbornene, 5-vinylnorbornene, 2,5-norbornadiene, dicyclopentadiene (DCPD) and vinylcyclohexene, preferably from the group consisting of 5-ethylidene-2-norbornene and 5-vinylnorbornene are made with metal complex of the present invention.

The invention further relates to polymers obtainable with the metal complex of the present invention or the catalyst system of the present invention. Below, the invention will be elucidated on the basis of the following examples and comparative experiments, without being limited thereto.

EXAMPLES

Test Methods
    Size Exclusion Chromatography (SEC) coupled to Refractive Index (RI) and Differential Viscometry (DV) detection. (SEC-DV)
Equipment:
    PL220 (Polymer Laboratories) SEC with PL220 DRI concentration detector and
    Viscotek 220R viscometry detector.
    Detectors are operated in parallel configuration.
    Degasser. PL-DG 802
Data processing:
    Viscotek data processing software, TriSEC 2.7 or higher version
Columns:
    PLgel Olexis (4×)
Calibration:
    Universal calibration with linear polyethylene (PE) standard (molecular weight 0.4-4000 kg/mol)
Temperature:
    160° C.
Flow:
    1.0 ml/min
Injection volume:
    0.300 ml
Solvent/eluent:
    Distilled 1,2,4-trichlorobenzene with about 1 g/l of Ionol stabilizer
Sample preparation:
    Dissolving for 4 hours at approx. 150° C.
    Filtration through 1.2 micron Ag filter
    Sample concentration approx. 1.0 mg/ml
    Intrinsic Viscosity (IV) was measured at 135° C. in decahydronaphtalen as solvent
NMR ($^1H$, 300 MHz, $^{13}C$ 75.4 MHz) spectra were measured on a Varian Mercury-VX 300 spectrometer.

Fourier transformation infrared spectroscopy (FT-IR), was used to determine the composition of the copolymers according to the method that is known in the art. The FT-IR measurement gives the composition of the various monomers in weight per cents relative to the total composition.

Part I: Synthesis of Ligands and Compounds
General

All manipulations were carried out using standard Schlenk line or dry-box techniques under an atmosphere of argon or dinitrogen. Solvents were degassed by sparging with dinitrogen and dried by passing through a column of the appropriate drying agent. Toluene was refluxed over sodium and distilled. Deuterated solvents were dried over potassium ($C_6D_6$) or $P_2O_5$ ($CDCl_3$ and $CD_2Cl_2$), distilled under reduced pressure and stored under dinitrogen in Teflon valve ampoules. NMR samples were prepared under dinitrogen in 5 mm Wilmad 507-PP tubes fitted with J. Young Teflon valves. $^1H$ and $^{13}C$-$\{^1H\}$ spectra were recorded on a Varian Mercury-VX 300 spectrometer at ambient temperature unless stated otherwise and referenced internally to residual protio-solvent ($^1H$) or solvent ($^{13}C$) resonances, and are reported relative to tetramethylsilane (d=0 ppm). Assignments were confirmed using two dimensional $^1H$-$^1H$ and $^{13}C$-$^1H$ NMR correlation experiments. Chemical shifts are quoted in δ (ppm) and coupling constants in Hz. Mass spectra were recorded by the mass spectrometry service of the University of Oxford. IR spectra were recorded on Nicolet Magna 560 E.S.P. FTIR, Perkin-Elmer 1710 or (for air-stable, solid samples) Bruker Tensor 27 FT-IR (thin film deposition on diamond ATR module) spectrometers. Air-sensitive samples were prepared in a dry-box as Nujol mulls between NaCl plates, and the data are quoted in wavenumbers ($cm^{-1}$) within the range 4000-400 $cm^{-1}$.

FIGURES

FIG. 1 shows the X-ray structure of compound 2
FIG. 2 shows the X-ray structure of compound 3
FIG. 3 shows the X-ray structure of compound 5
FIG. 4 shows the X-ray structure of compound 6
FIG. 5 shows the X-ray structure of compound 8
FIG. 6 shows the X-ray structure of compound 9

SYNTHESIS OF COMPOUNDS FOR THE COMPARATIVE EXAMPLES

Compound A ($Me_5CpTiCl_2(NC(Ph)(iPr_2N))$) was prepared as described for compound 6 in WO 2005/090418.

Synthesis of $Me_5CpTiMe_2(NC(Ph)(iPr_2N))$ (Compound B)

To a stirring toluene (15 mL) solution of Cp*Ti{NC(Ph)N$^i$Pr$_2$}Cl$_2$ (3) (1.00 g, 2.20 mmol) was added dropwise MeLi (2.80 mL, 1.6 M in Et$_2$O, 4.40 mmol) and the resulting solution was stirred for 16 h. The volatiles were then removed in vacuo and the yellow solid was then extracted into n-hexanes (50 mL). Concentration of the solution to ca. 15 mL and subsequent storage at −30° C. for 24 h resulted in crystallisation of the desired product as large yellow crystals which were isolated and dried in vacuo. Yield=0.37 g (40%). The product was characterized by $^1H$-NMR and $^{13}C$-NMR.

(B)

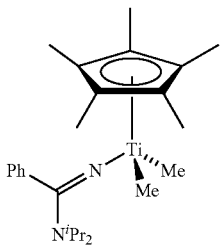

Compound C {η⁵,η¹-C₅Me₄-2-C₅H₄C(ᵗBu)N}TiCl₂ was prepared as described in EP1426379B1, example 48.

(C)

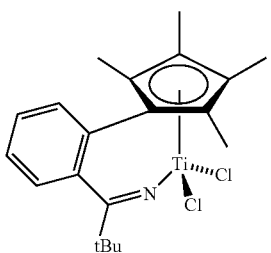

Compound D

To a stirring hexanes solution (15 mL) of Compound C (0.27 g) was added dropwise two equivalents of MeMgCl (0.5 mL, 3.0 in THF). The solution rapidly turned from green to red with precipitation of colourless salts. After stirring for 2 h the volatiles were removed in vacuo and the resulting solid extracted in to hexanes and filtered. The hexanes were then removed in vacuo and the oily material carefully dried giving the desired product as a bright red waxy solid. Yield=0.065 g (27%). The compound was characterized by ¹H NMR (300 MHz) (C₆D₆) δ (ppm): 7.7 (d, 1H), 7.2 (d, 1H), 7.1 (dd, 1H) 7.0 (dd, 1H), 2.1 (s, 6H), 1.5 (s, 6H), 1.4 (s, 9H), 0.7 (s, 6H) and by ¹³C-NMR (75.5 MHz) (CDCl₃) δ (ppm): 186.0, 141.9, 138.4, 133.3, 133.0, 129.7, 129.3, 127.2, 126.5, 121.4, 51.5, 31.3, 31.1, 12.8, 12.1.

(D)

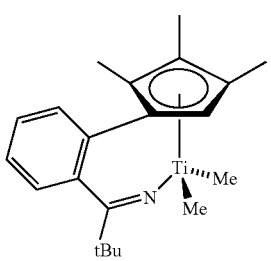

Synthesis of Compounds for the Examples of the Invention

Synthesis of C₅Me₄H-2-C₆H₄C(NMe₂)NH (Compound 1)

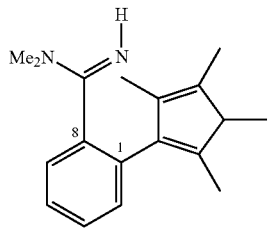 [SMILES: [H]/N=C(/c1ccccc1C1=C(C)C(C)C(C)=C1C)N(C)C]

To a stirring THF (80 mL) solution of LiNMe₂ (8.26 g, 162 mmol) cooled to −78° C. was added dropwise a solution of C₅Me₄H-2-C₆H₄CN (6.03 g, 27 mmol) in THF (60 mL). Following slow warming to RT, the solution had turned a very dark colour. The solution was then stirred at RT for a further 16 h after which time the solution had turned dark red. Toluene (100 mL) followed by water (200 mL) was added to quench the reaction, the aqueous phase was removed and the organic layer was dried over MgSO₄. The solvent was removed in vacuo affording a viscous orange oil which was triturated with pentane and dried in vacuo giving a waxy orange solid. Yield=6.86 g (95%). ¹H NMR (major isomer (80%)) (CD₂Cl₂, 299.9 MHz, 243 K): 7.50-7.16 (4H, series of overlapping m, Ar), 3.16 (3H, as, N$\underline{Me_2}$)), 2.87 (1H, br q, C$\underline{H}$Me, ³J=7.1 Hz), 2.54 (3H, s, N$\underline{Me_2}$), 1.88 (3H, br s, CMeC$\underline{Me}$CHMe), 1.84 (3H, br s, CHMeC$\underline{Me}$CAr), 1.38 (3H, s, CMeC$\underline{Me}$CAr), 0.79 (3H, d, CH$\underline{Me}$, ³J=7.1 Hz) ppm (NH not observed). ¹³C-{¹H} NMR (major isomer) (CD₂Cl₂, 75.4 MHz, 243 K): 166.3 ($\underline{C}$N(NMe₂)), 142.5 (C$\underline{Me}$$\underline{C}$MeCHMe), 140.6 (CHMe$\underline{C}$MeCAr), 136.0 ($\underline{C}$Ar), 134.4 (CMe$\underline{C}$MeCAr), 131.4 (Ar $\underline{C}$H), 130.9 (Ar CH), 129.0 (1-C₆H₄ or 6-C₆H₄), 127.0 (Ar CH), 126.9 (Ar CH), 125.7 (6-C₆H₄ or 1-C₅H₄), 50.5 ($\underline{C}$HMe), 40.4 (N$\underline{Me_2}$), 39.6 (N $\underline{Me_2}$), 15.0 (CH$\underline{Me}$), 12.5 (CMeC$\underline{Me}$CHMe), 12.0 (CMeC $\underline{Me}$CAr), 11.2 (CHMeC$\underline{Me}$CAr) ppm. IR (thin film, cm⁻¹): 3383 (s, u(N—H)), 2957 (m), 2870 (m), 1632 (s), 1461 (m), 1453 (m), 1432 (w), 1349 (w), 1251 (s), 1128 (m), 1026 (m), 821 (m), 720 (s). FI-HRMS: m/z=268.1938 (calcd. for [C₁₈H₂₄N₂]⁺ m/z=268.1939).

Synthesis of {η⁵,η¹-C₅Me₄-2-C₆CH₄C(NMe₂) N}TiCl₂ (Compound 2)

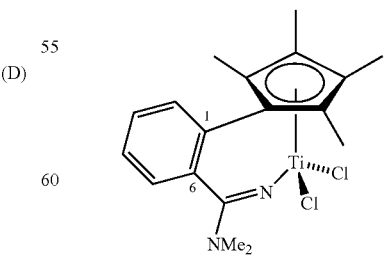

To a stirring toluene (40 mL) solution of Ti(NMe₂)₄ (6.10 mL, 25.6 mmol) was added dropwise a toluene (20 mL) solution of C₅Me₄H-2-C₆H₄C(NMe₂)NH (Compound 1)

(6.86 g, 25.6 mmol). The solution immediately turned from orange to dark red and was stirred for a further 6 h at RT. The volatiles were then removed in vacuo and the solid extracted into toluene (40 mL). Trimethylsilyl chloride (7.10 mL, 56.3 mmol) was added dropwise and the solution was stirred for a further 16 h. The volatiles were again removed in vacuo and the dark red solid extracted into warm (ca. 50° C.) toluene (80 mL). The desired product crystallized after storage at −30° C. for two days. Following washing thoroughly with pentane (4×20 mL) and drying in vacuo the product was isolated as an orange microcrystalline powder. Yield=4.48 g (45%). $^1$H NMR (CD$_2$Cl$_2$, 299.9 MHz, 293 K): 7.64-7.46 (4H, series of overlapping m, Ar), 3.34 (3H, s, NMe$_2$), 3.14 (3H, s, NMe$_2$), 2.19 (6H, s, C$\underline{Me}$CMeCAr), 1.73 (6H, s, CMeC$\underline{Me}$CAr) ppm. $^{13}$C-{$^1$H} NMR (CD$_2$Cl$_2$, 75.4 MHz, 293 K): 168.8 (CN), 138.7 (1-C$_6$H$_4$), 135.8 (6-C$_6$H$_4$), 132.0 (Ar CH), 131.3 (Ar CH), 130.7 (C$\underline{Me}$CMeCAr), 128.7 (CMe$\underline{C}$MeCAr), 127.7 (Ar CH), 127.5 (Ar CH), 125.1 ($\underline{C}$Ar), 41.7 (NMe$_2$), 40.1 (NMe$_2$), 13.1 (CMe$\underline{Me}$CAr), 12.4 (C$\underline{Me}$CMeCAr) ppm. IR (NaCl plates, Nujol mull, cm$^{-1}$): 1573 (s), 1547 (s), 1269 (m), 1248 (m), 1206 (m), 1079 (w), 1019 (m), 953 (w), 918 (w), 880 (m), 823 (s), 774 (w), 760 (s), 712 (m), 673 (w), 595 (m), 536 (m). Anal. found (calcd. for C$_{18}$H$_{22}$Cl$_2$N$_2$Ti.0.1 (C$_7$H$_8$)): C, 56.98 (56.95); H, 5.82 (5.83); N, 7.02 (7.10) %. EI-MS: m/z=384 (30%, [M]$^+$), 340 (20%, [M−NMe$_2$]$^+$). Single crystals suitable for X-ray diffraction were grown from a benzene solution at room temperature.

Synthesis of {η$^5$,η$^1$-C$_5$Me$_4$-2-C$_6$H$_4$C(NMe$_2$)N}TiMe$_2$ (Compound 3)

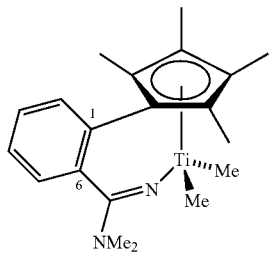

To a stirring toluene (40 ml) solution of {η$^5$,η$^1$-C$_5$Me$_4$-2-C$_6$H$_4$C(NMe$_2$)N}TiCl$_2$ (Compound 2) (1.0 g, 2.60 mmol) was added dropwise two equivalents of MeMgCl (1.73 mL, 3.0 M in THF, 5.20 mmol). Following stirring for 16 h, the volatiles were removed in vacuo and the resulting solid extracted into pentane (4×20 mL). The desired complex was recrystallised from a concentrated pentane solution (20 mL) at −30° C. as a yellow-brown powder which was isolated and dried in vacuo. Yield=0.27 g (30%). $^1$H NMR (C$_6$D$_6$, 299.9 MHz, 293 K): 7.29 (1H, d, 2-C$_6$H$_4$, $^3$J=7.7 Hz), 7.09 (1H, dd, 3-C$_6$H$_4$, $^3$J=7.7 Hz, 7.8 Hz), 6.95 (1H, dd, 4-C$_5$H$_4$, $^3$J=6.5 Hz, 7.8 Hz), 6.93 (1H, d, 5-C$_6$H$_4$, $^3$J=6.5 Hz), 2.65 (6H, s, NMe$_2$), 2.19 (6H, s, C$\underline{Me}$CMeCAr), 1.51 (6H, s, CMeC$\underline{Me}$CAr), 0.60 (6H, s, TiMe) ppm. $^{13}$C-{$^1$H} NMR (C$_6$D$_6$, 75.4 MHz, 293 K): 166.3 (CN), 138.6 (1-C$_6$H$_4$), 138.5 (6-C$_6$H$_4$), 132.0 (2-C$_6$H$_4$), 129.0 (3-C$_6$H$_4$), 126.8 (4-C$_6$H$_4$), 125.6 (5-C$_6$H$_4$), 123.8 (CMe$\underline{C}$MeCAr), 120.5 (C$\underline{Me}$CMeCAr), 119.0 ($\underline{C}$Ar), 43.9 (TiMe), 39.2 (NMe$_2$), 11.9 (CMe$\underline{Me}$CAr), 11.7 (C$\underline{Me}$CMeCAr) ppm. IR (NaCl plates, Nujol mull, cm$^{-1}$): 1596 (e), 1570 (s), 1560, 918 (m), 817 (s), 774 (m), 757 (s), 714 (m), 678 (m), 643 (w). Anal. found (calcd. for C$_{20}$H$_{28}$N$_2$Ti): C, 69.82 (69.77); H, 8.34 (8.20); N, 7.92 (8.14) %. EI-MS: m/z=329 (5%, [M−Me]$^+$), 314 (40%, [M-2Me]$^+$), 270 (20%, [M-2Me−NMe$_2$]$^+$). Single crystals suitable for X-ray diffraction were grown from a pentane solution at room temperature.

Synthesis of C$_5$Me$_4$H-2-C$_6$H$_4$C(N$^i$Pr$_2$)NH (Compound 4)

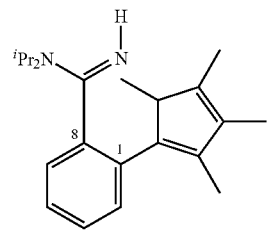

To a stirring THF (60 mL) solution of diisopropylamine (11.5 mL, 81 mmol) cooled to −7820° C. was added dropwise MeMgBr (27 mL, 3.0 M in Et$_2$O, 81 mmol). The resulting white suspension was allowed to warm slowly to RT. Following 10 min stirring at RT, the suspension was cooled to −78° C. and a solution of C$_5$Me$_4$H-2-C$_6$H$_4$CN (3.02 g, 13.5 mmol) in THF (40 mL) was added dropwise. Following slow warming to RT, the solution had turned dark red-brown. The solution was then stirred at RT for a further 16 h after which time the solution had turned dark red. Toluene (100 mL) followed by water (200 mL) was added to quench the reaction, the aqueous phase was removed and the organic layer was dried over MgSO$_4$. The solvent was removed in vacuo giving a viscous orange oil. The crude product was purified by silica gel column chromatography (5-10% n-hexanes in Et$_2$O). Yield=2.22 g (51%).

Alternative Preparation of Compound 4

To a stirring THF (50 mL) solution of HN$^i$Pr$_2$ (5.5 mL, 39.2 mmol) was added dropwise MeMgCl (13.1 mL, 3.0 M in THF, 39.2 mmol). The solution was stirred for 5 h at 60° C. resulting in formation of a colourless precipitate. The suspension was then cooled to −78° C. and a THF (25 mL) solution of C$_5$Me$_4$H-2-C$_6$H$_4$C(H)NOMe (1.0 g, 3.92 mmol) was added dropwise. The solution was slowly warmed to RT and stirred for 3 days. The reaction was quenched by slow, dropwise addition of water (1 mL), after 1.5 h the orange suspension was filtered. The solids were washed with Et$_2$O (10×25 mL). The organic phase was then dried over anhydrous magnesium sulphate and the volatiles were removed in vacuo affording Compound 4 (0.95 g (75%)) as an orange oil.

$^1$H NMR (major isomer (70%)) (CDCl$_3$, 299.9 MHz, 293 K): 7.34-7.08 (4H, series of overlapping m, Ar), 3.62 (1H, sept, N(C$\underline{H}$Me$_2$)$_2$, $^3$J=6.5 Hz), 3.44 (1H, br q, C$\underline{H}$Me, $^3$J=7.5 Hz), 3.19 (1H, sept, N(C$\underline{H}$Me$_2$)$_2$, $^3$J=6.5 Hz), 1.85 (3H, s, CMeC$\underline{Me}$CMe), 1.83 (3H, s, CMeC$\underline{Me}$CAr), 1.67 (3H, br s, CMeC$\underline{Me}$CHMe), 1.08 (6H, d, N(CH$\underline{Me}$$_2$), $^3$J=6.5 Hz), 0.87 (3H, d, CH$\underline{Me}$, $^3$J=7.5 Hz), 0.74 (6H, d, N(CH$\underline{Me}$$_2$), $^3$J=6.5 Hz) ppm (NH not observed). $^{13}$C-{$^1$H} NMR (major isomer) (CDCl$_3$, 75.4 MHz, 293 K): 158.8 $\underline{C}$N(N$^i$Pr$_2$), 141.6 (CMe$\underline{C}$MeCMe), 139.7 ($\underline{C}$Ar), 138.2 (1-C$_6$H$_4$ or 6-C$_6$H$_4$), 137.6 (CMe$\underline{C}$MeCMe), 133.6 (CMe$\underline{C}$MeCAr), 130.7 (Ar CH), 128.2 (6-C$_6$H$_4$ or 1-C$_6$H$_4$), 127.2 (Ar CH), 126.7 (Ar CH), 126.2 (Ar CH), 51.5 (N(C$\underline{H}$Me$_2$)$_2$), 51.4 (N(C$\underline{H}$Me$_2$)$_2$), 51.0 ($\underline{C}$HMe), 15.3 (N(CH$\underline{Me}$$_2$)$_2$), 15.1 (CH$\underline{Me}$), 14.2 (N(CH Me$_2$)$_2$), 12.3 (CMe CMeCHMe), 12.1 (CMeCMeCMe), 11.3 (CMeCMeCAr) ppm. IR (thin film, cm$^{-1}$): 3389 (s, υ(N—H)), 2962 (s), 2855 (s), 2753 (m), 1953 (m), 1697 (s), 1621 (s), 1573 (s), 1447 (m), 1367 (m), 1260 (m), 1179 (w), 1026 (s), 921 (w), 802 (s), 761 (s), 733 (m), 699 (m), 680 (w). ESI$^+$-HRMS: m/z=325.2638 (calcd. for [C$_{22}$H$_{33}$N$_2$]$^+$ m/z=325.2638).

Synthesis of {η$^5$,η$^1$-C$_5$Me$_4$-2-C$_6$H$_4$C(N$^i$Pr$_2$)N}TiCl$_2$ (Compound 5)

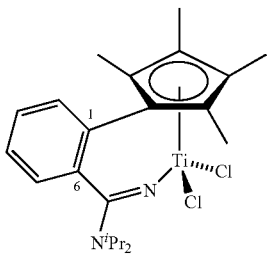

To a stirring toluene (30 mL) solution of Ti(NMe$_2$)$_4$ (1.60 mL, 6.90 mmol) was added dropwise a toluene (20 mL) solution of C$_5$Me$_4$H-2-C$_6$H$_4$C(N$^i$Pr$_2$)NH (Compound 4) (2.22 g, 6.90 mmol). The solution immediately turned from orange to dark red and was stirred for a further 6 h at RT. The volatiles were then removed in vacuo and the solid extracted into toluene (40 mL). Trimethylsilyl chloride (1.90 mL, 15.2 mmol) was added dropwise and the solution was stirred for a further 16 h. The volatiles were again removed in vacuo and the dark red solid extracted into benzene (25 mL). The desired product crystallised as a red/orange solid from the concentrated benzene solution (15 mL) and, after washing thoroughly with pentane (4×20 mL), was isolated and dried in vacuo. Yield=1.84 g (61%). $^1$H NMR (Toluene-d$_8$, 299.9 MHz, 213 K): 7.15-7.00 (4H, series of overlapping m, Ar), 3.73 (1H, sept, CHMe$_2$ cis to Ar, $^3$J=6.0 Hz), 2.75 (1H, sept, CHMe$_2$ trans to Ar, $^3$J=6.3 Hz), 2.23 (6H, s, CMeCMeCAr), 1.97 (3H, s, CMeCMeCAr (closer to Ar)), 1.60 (6H, br s, two peaks overlapping: 3H, d, CHMe$_2$ trans to Ar and 3H, s, CMeCMeCAr (further from Ar)), 1.41 (3H, d, CHMe$_2$ trans to Ar, $^3$J=5.9 Hz), 0.76 (3H, br d, CHMe$_2$ cis to Ar, $^3$J=6.0 Hz), 0.43 (3H, br d, CHMe$_2$ cis to Ar, $^3$J=6.0 Hz) ppm. $^{13}$C-{$^1$H} NMR (Toluene-d$_6$, 75.4 MHz, 213 K): 167.6 (CN), 139.0 (1-C$_6$H$_4$), 138.1 (6-C$_6$H$_4$), 132.0 (Ar CH), 130.6 (Ar CH), 129.9 (Ar CH), 128.0 (MeCMeCAr), 127.2 (CMeCMeCAr), 126.6 (CMeCMeCAr (further from Ar)), 126.4 (CMeCMeCAr (closer to Ar)), 126.1 (Ar CH), 124.1 (CAr), 53.6 (CHMe$_2$ cis to Ar), 48.2 (CHMe$_2$ trans to Ar), 20.8 (CHMe$_2$ cis to Ar), 20.3 (two peaks overlapping: CHMe$_2$ cis to Ar and CHMe$_2$ trans to Ar), 18.5 (CHMe$_2$ trans to Ar), 14.7 (CMeCMeCAr (closer to Ar)), 13.0 (CMeCMeCAr (further from Ar)), 12.2 (CMeCMeCAr), 11.7 (CMeCMeCAr) ppm. IR (NaCl plates, Nujol mull, cm$^{-1}$): 1595 (w), 1569 (w), 1304 (s), 1261 (s), 1151 (m), 1083 (m), 1018 (s), 966 (w), 890 (m), 801 (m), 771 (m). Anal. found (calcd. for C$_{22}$H$_{30}$Cl$_2$N$_2$Ti.0.1 (C$_6$H$_6$)): C, 60.30 (60.45); H, 6.84 (6.87); N, 5.60 (6.24) %. EI-MS: m/z=440 (3%, [M]$^+$), 397 (100%, [M-$^i$Pr]$^+$), 340 (70%, [M-N$^i$Pr$_2$]$^+$), 305 (30%, [M-N$^i$Pr$_2$-Cl]$^+$), 222 (50%, [M-TiCl$_2$-N$^i$Pr$_2$]$^+$), 78 (100%, [Ph]$^+$). Single crystals suitable for X-ray diffraction were grown from a benzene solution at room temperature.

Synthesis of {η$^5$,η$^1$-C$_5$Me$_4$-2-C$_6$H$_4$C(N$^i$Pr$_2$)N}TiMe$_2$ (Compound 6)

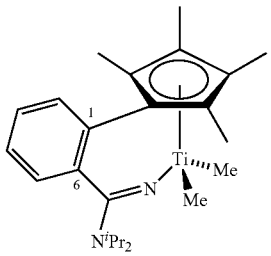

To a stirring toluene (30 mL) solution of {η$^5$,η$^1$-C$_5$Me$_4$-2-C$_6$H$_4$C(N$^i$Pr$_2$)N}TiCl$_2$ (Compound 5) (0.66 g, 1.50 mmol) was added dropwise two equivalents of MeMgCl (1.00 mL, 3.0 M in THF, 3.00 mmol). Following stirring for 16 h, the volatiles were removed in vacuo and the resulting solid extracted into pentane (4×20 mL). The desired complex was recrystallised from a concentrated pentane solution (20 mL) at −30° C. as a yellow powder which was isolated and dried in vacuo. Yield=0.24 g (40%). $^1$H NMR (C$_6$D$_6$, 299.9 MHz, 293 K): 7.34 (1H, d, 2-C$_6$H$_4$, $^3$J=7.6 Hz), 7.14 (1H, d, 5-C$_6$H$_4$, $^3$J=7.8 Hz), 7.08 (1H, dd, 3-C$_6$H$_4$, $^3$J=7.5 Hz, 7.6 Hz), 6.93 (1H, dd, 4-C$_6$H$_4$, $^3$J=7.5 Hz, 7.8 Hz), 3.47 (2H, br sept, CHMe$_2$, $^3$J=6.0 Hz), 2.20 (6H, s, CMeCMeCAr), 1.64 (6H, s, CMeCMeCAr), 1.28 (12H, br d, CHMe$_2$, $^3$J=6.0 Hz), 0.52 (6H, s, TiMe) ppm. $^{13}$C-{$^1$H} NMR (C$_6$D$_6$, 75.4 MHz, 293 K): 165.8 (CN), 141.6 (1-C$_6$H$_4$), 138.5 (6-C$_6$H$_4$), 132.8 (2-C$_6$H$_4$), 128.7 (3-C$_6$H$_4$), 125.8 (5-C$_1$H$_4$), 125.3 (4-C$_6$H$_4$), 123.6 (CMeCMeCAr), 120.4 (CAr), 119.4 (CMeCMeCAr), 50.0 (TiMe), 45.9 (CHMe$_2$)), 21.1 (CHMe$_2$), 12.5 (CMeCMeCAr), 11.7 (CMeCMeCAr) ppm. IR (NaCl plates, Nujol mull, cm$^{-1}$): 1570 (w), 1524 (s), 1313 (s), 1220 (w), 1024 (m), 889 (w), 783 (m), 758 (m), 674 (w). Anal. found (calcd. for C$_{24}$H$_{36}$N$_2$Ti): C, 71.65 (71.99); H, 8.84 (9.06); N, 6.89 (7.00) %. EI-MS: m/z=385 (5%, [M−Me]$^+$), 370 (40%, [M-2Me]$^+$), 270 (75%, [M-2Me−N$^i$Pr$_2$]$^+$). Single crystals suitable for X-ray diffraction were grown from benzene solution at room temperature.

Synthesis of C$_5$Me$_4$H-2-C$_6$H$_4$C(NCy$_2$)NH (Compound 7)

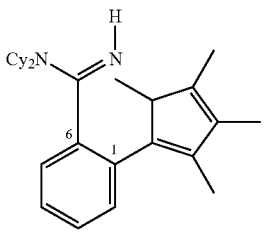

To a stirring THF (100 mL) solution of dicyclohexylamine (26.9 mL, 135 mmol) cooled to −78° C. was added dropwise MeMgBr (45 mL, 3.0 M in Et$_2$O, 135 mmol). The resulting yellow solution was allowed to warm slowly to RT. Following 10 min stirring at RT, the solution was cooled to −78° C. and a solution of C$_5$Me$_4$H-2-C$_6$H$_4$CN (5.02 g, 22.5 mmol) in THF (40 mL) was added dropwise. Following slow warming to RT, the solution had turned dark red-brown. The solution was then stirred at RT for a further 16 h after which time the solution had turned dark red. Water (400 mL) was added to quench the reaction, the aqueous phase was removed and the organic layer was dried over MgSO$_4$. The volatiles were removed in vacuo affording a viscous orange oil. The crude product was purified by silica gel column chromatography (5-10% n-hexanes, 5% HN$^i$Pr, in Et$_2$O). Yield=3.07 g (34%). $^1$H NMR (major isomer (70%)) (CDCl$_3$, 299.9 MHz, 293 K): 7.31-7.08 (4H, series of overlapping m, Ar), 5.78 (1H, s, NH), 3.46 (1H, qn, C$\underline{H}$C$_5$H$_{10}$, $^3$J=7.0 Hz), 3.44 (1H, br q, C$\underline{H}$Me, $^3$J=7.5 Hz), 2.99 (1H, br m, C$\underline{H}$C$_5$H$_{10}$), 1.85 (3H, s, CMeC$\underline{Me}$CMe), 1.82 (3H, s, CMeC$\underline{Me}$CAr), 1.60 (3H, br s, CMeC$\underline{Me}$CHMe), 1.74-0.91 (20H, series of overlapping m for CHC$_5$H$_{10}$), 0.86 (3H, d, CH$\underline{Me}$, $^3$J=7.5 Hz) ppm. $^{13}$C-{$^1$H} NMR (major isomer) (CDCl$_3$, 75.4 MHz, 293 K): 168.3 $\underline{C}$N(NCy$_2$), 142.7 (CMe$\underline{C}$MeCHMe), 141.6 ($\underline{C}$Ar), 138.2 (1-C$_6$H$_4$ or 6-C$_6$H$_4$), 133.3 (CMe$\underline{C}$MeCMe), 131.1 (CMe$\underline{C}$MeCAr), 128.6 (Ar CH), 128.2 ($\overline{6}$-CH$_4$ or 1-C$_6$H$_4$), 127.5 (Ar CH), 127.0 (Ar CH), 126.5 (Ar CH), 59.7 ($\underline{C}$HC$_5$H$_{10}$), 51.2 ($\underline{C}$HMe), 46.3 ($\underline{C}$HC$_5$H$_{10}$), 28.1 (CH$\underline{C}$$_5$H$_{10}$), 26.9 (CH$\underline{C}$$_5$H$_{10}$), 26.8 (CH$\underline{C}$$_5$H$_{10}$), 26.5 (CH$\underline{C}$$_5$H$_{10}$), 26.3 (CH$\underline{C}$$_5$H$_{10}$), 26.2 (CH$\underline{C}$$_5$H$_{10}$), 25.6 (CH$\underline{C}$$_5$H$_{10}$), 25.5 (CH$\underline{C}$$_5$H$_{10}$), 22.8 (CH$\underline{C}$$_5$H$_{10}$), 22.7 (CH$\underline{C}$$_5$H$_{10}$), 15.4 (CH$\underline{Me}$), 12.8 (CMeC$\underline{Me}$CHMe), 12.0 (CMeC$\underline{Me}$CMe), 11.2 (CMeC$\underline{Me}$CAr) ppm. IR (thin film, cm$^{-1}$): 3311 (s, u(N—H)), 3057 (m), 2926 (s), 2853 (s), 1702 (s), 1573 (s), 1484 (m), 1446 (s), 1379 (s), 1326 (m), 1273 (m), 1255 (m), 1194 (s), 1125 (s), 1042 (w), 991 (m), 920 (w), 894 (m), 841 (w), 812 (w), 760 (s), 716 (w), 972 (m), 602 (m). ESI$^+$-HRMS: m/z=405.3250 (calcd. for [C$_{29}$H$_{41}$N$_2$]$^+$ m/z=405.3264).

Synthesis of {η$^5$,η$^1$-C$_5$Me$_4$-2-C$_6$H$_4$C(NCy$_2$)N}TiCl$_2$ (Compound 8)

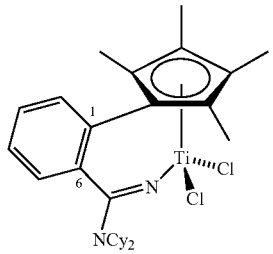

To a stirring toluene (30 mL) solution of Ti(NMe$_2$)$_4$ (1.80 mL, 7.59 mmol) was added dropwise a toluene (20 mL) solution of C$_5$Me$_4$H-2-C$_6$H$_4$C(NCy$_2$)NH (Compound 7) (3.07 g, 7.59 mmol). The solution immediately turned from orange to dark red and was stirred for a further 6 h at RT. The volatiles were then removed in vacuo and the solid extracted into toluene (40 mL). Trimethylsilyl chloride (2.60 mL, 20.4 mmol) was added dropwise and the solution was stirred for a further 16 h. The volatiles were again removed in vacuo and the dark red solid washed with pentane (3×20 mL) and subsequently extracted into hot toluene (60 mL). The desired product crystallized after storage for 16 h at −30° C. The crystals were washed with pentane (3×20 mL) and dried in vacuo. Yield=1.26 g (32%). $^1$H NMR (CD$_2$Cl$_2$, 299.9 MHz, 293 K): 7.60-7.39 (4H, series of overlapping m, Ar), 3.92 (1H, br m, C$\underline{H}$C$_5$H$_{10}$), 2.98 (1H, br m, C$\underline{H}$C$_5$H$_{10}$), 2.16 (6H, s, CMeC$\underline{Me}$CMeCAr), 1.91-1.10 (20H, series of overlapping m for CHC$_5$H$_{10}$), 1.81 (6H, s, CMeC$\underline{Me}$CAr) ppm. $^{13}$C-{$^1$H} NMR (CD$_2$Cl$_2$, 75.4 MHz, 293 $\overline{K}$): 168.7 (CN), 138.9 (1-C$_6$H$_4$), 138.5 (6-C$_6$H$_4$), 132.6 (Ar CH), 130.5 (Ar CH), 129.3 ($\underline{C}$MeCMeCAr), 128.5 (CMe$\underline{C}$MeCAr), 126.8 (Ar CH), 126.3 (Ar CH), 125.3 ($\underline{C}$Ar), 63.2 ($\underline{C}$HC$_5$H$_{10}$), 59.7 ($\underline{C}$HC$_5$H$_{10}$), 32.5 (CH$\underline{C}$$_5$H$_{10}$), 32.3 (CH$\underline{C}$$_5$H$_{10}$), 28.9 (CH$\underline{C}$$_5$H$_{10}$), 28.7 (CH$\underline{C}$$_5$H$_{10}$), 26.7 (CH$\underline{C}$$_5$H$_{10}$), 26.6 (CH$\underline{C}$$_5$H$_{10}$), 26.5 (CH$\underline{C}$$_5$H$_{10}$), 26.1 (CH$\underline{C}$$_5$H$_{10}$), 25.9 (CH$\underline{C}$$_5$H$_{10}$), 25.4 (CH$\underline{C}$$_5$H$_{10}$), 13.6 (CMeC$\underline{Me}$CAr), 12.2 (C$\underline{Me}$CMeCAr) ppm. IR (NaCl plates, Nujol mull, cm$^{-1}$): 1569 (m), 1504 (s), 1332 (m), 1317 (s), 1260 (m), 1249 (w), 1160 (w), 1018 (m), 992 (s), 895 (m), 830 (s), 781 (m), 759 (s), 709 (w), 691 (m), 646 (w). Anal. found (calcd. for C$_{28}$H$_{38}$Cl$_2$N$_2$Ti): C, 64.67 (64.50); H, 7.35 (7.35); N, 5.15 (5.37) %. EI-MS: m/z=520 (3%, [M]$^+$), 437 (100%, [M−Cy]$^+$), 340 (60%, [M−NCy$_2$]$^+$), 305 (40%, [M−Cl−NCy$_2$]$^+$). Single crystals suitable for X-ray diffraction were grown by slow cooling of a benzene solution from 70° C. to room temperature.

Synthesis of {η$^5$,η$^1$-C$_5$Me$_4$-2-C$_6$H$_4$C(NCy$_2$)N}TiMe$_2$ (Compound 9)

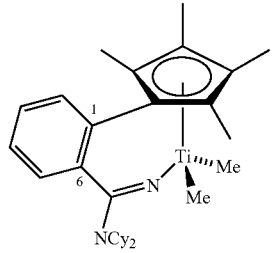

To a stirring toluene (30 mL) solution of {η$_5$,η$^1$-C$_5$Me$_4$-2-C$_6$H$_4$C(NCy$_2$)N}TiCl$_2$ (Compound 8) (1.00 g, 1.92 mmol) was added dropwise two equivalents of MeLi (2.40 mL, 1.6 M in Et$_2$O, 3.84 mmol). Following stirring for 3 h, the volatiles were removed in vacuo and the resulting solid extracted into n-hexanes (4×20 mL). The desired complex was recrystallised from a concentrated n-hexanes solution (30 mL) at −30° C. as a yellow powder which was isolated and dried in vacuo. Yield=0.34 g (37%). $^1$H NMR (C$_6$D$_6$, 299.9 MHz, 293 K): 7.35 (1H, d, 2-C$_6$H$_4$, $^3$J=7.6 Hz), 7.21 (1H, d, Ar, 5-C$_6$H$_4$, $^3$J=7.8 Hz), 7.07 (1H, dd, 3-C$_6$H$_4$, $^3$J=7.4 Hz, 7.6 Hz), 6.93 (1H, dd, 4-C$_5$H$_4$, $^3$J=7.4 Hz, 7.8 Hz), 3.30 (2H, br m, C$\underline{H}$C$_5$H$_{10}$), 2.21 (6H, s, C$\underline{Me}$CMeCAr), 1.69 (6H, s, CMeC$\underline{Me}$CAr), 1.65-0.85 (20H, series of overlapping m for CHC$_5$$\underline{H}$$_{10}$), 0.53 (6H, s, TiMe) ppm. $^{13}$C-{$^1$H} NMR (C$_6$D$_6$, 75.4 MHz, 293 K): 166.0 (CN), 141.4 (1-C$_6$H$_4$), 138.6 (6-C$_6$H$_4$), 132.9 (2-C$_6$H$_4$), 128.7 (3-C$_6$H$_4$), 125.5 (5-C$_6$H$_4$), 125.2 (4-C$_6$H$_4$), 123.5 ($\underline{C}$MeCMeCAr), 120.5 ($\underline{C}$Ar), 119.5 (CMe$\underline{C}$MeCAr), 60.2 (br, $\underline{C}$HC$_5$H$_{10}$), 46.2 (TiMe), 32.0 (CH$\underline{C}$$_5$H$_{10}$), 31.4 (CH$\underline{C}$$_5$H$_{10}$), 25.8 (CH$\underline{C}$$_5$H$_{10}$), 23.1 (CH$\underline{C}$$_5$H$_{10}$), 14.3 (CH$\underline{C}$$_5$H$_{10}$), 12.7 (CMeC$\underline{Me}$CAr), 11.8 (C$\underline{Me}$CMeCAr) ppm. IR (NaCl plates, Nujol mull, cm$^{-1}$): 2360 (s), 2340 (m), 1304 (s), 1078 (m), 966 (m), 892 (w), 668 (s), 480 (s). Anal. found (calcd. for C$_{30}$H$_{44}$N$_2$Ti): C, 74.92 (74.98); H, 9.52 (9.23); N, 5.57 (5.83) %. EI-MS m/z 465 (3%, [M−Me]$^+$), 450 (25%, [M−2Me]$^+$), 270 (20%, [M−2Me−NCy$_2$]$^+$). Single crystals suitable for X-ray diffraction were grown from a benzene solution at room temperature.

Part II: Batch EPDM Co-Polymerisations (General Procedure)

The batch co-polymerizations were carried out in a 2-liter batch autoclave equipped with a double intermig and baffles.

The reaction temperature was set on 90+/−3° C. and controlled by a Lauda Thermostat. The feed streams (solvents and monomers) were purified by contacting with various adsorption media to remove catalyst killing impurities such as water, oxygen and polar compounds as is known to those skilled in the art. During polymerisation the ethylene and propylene monomers were continuously fed to the gas cap of the reactor. The pressure of the reactor was kept constant by a back-pressure valve.

In an inert atmosphere of nitrogen, the reactor was filled with pentamethylheptanes (PMH) (950 mL), MAO-10T (Crompton, 10 wt % in toluene), BHT, 5-ethylidene-2-norbonene (ENB) (0.7 mL), 5-vinyl-2-norbonene (VNB) (0.7 mL) and dicyclopentadiene (DCPD) (0.7 mL) respectively. The reactor was heated to 90° C., while stirring at 1350 rpm. The reactor was pressurized and conditioned under a determined ratio of ethylene, propylene and hydrogen (0.35 NL/h) After 15 minutes, the catalyst components were added into the reactor and the catalyst vessel was rinsed with PMH (50 mL) subsequently. (When TBF20 was used; the borate was added directly after the catalyst was added). After 10 minutes of polymerisation, the monomer flow was stopped and the solution was carefully dumped in an Erlenmeyer flask of 2 L, containing a solution of Irganox-1076 in iso-propanol and dried over night at 100° C. under reduced pressure. The polymers were analysed for intrinsic viscosity (IV), for molecular weight distribution (SEC-DV) and composition (FT-IR).

The experimental conditions and results are given in table 1.

formation in this range. Even though the catalyst amount might be different the data can be used to establish certain results.

The parameter to look at are preferably the Mw and Mz values as they show what molecular weight magnitudes were achievable. As higher temperatures normally give a lower Mw or Mz value the above mentioned lower amount of catalyst in order to limit the temperature to about 90° C. would in case of the same amount lead to higher temperatures which give lower Mw and Mz values which would even amplify this effect rather than to compensate this effect.

The inventive compounds lead to higher Mw values than possible with R1=alkyl (see compounds C and D) known from EP1426379B1.

What is claimed is:
1. A metal complex of the formula (1)

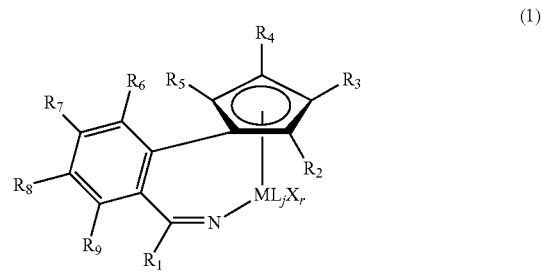

(1)

| Example | Metal-organic Compound | MAO (µmol) | Metal-organic compound dosage (µmol) | Yield (g) | Residual Ti in polymer (ppm)[1] | Incorporated C2 (wt %) | ENB (wt %) | VNB (wt %) | DCPD (wt %) | IV (dl/g) | Mw (kg/mol) | Mz (kg/mol) | Mw/Mn |
|---|---|---|---|---|---|---|---|---|---|---|---|---|---|
| 5[3] | 6 | 450 | 0.25 | 5.9 | 2.0 | 40 | 0 | 0 | 0 | 3.1 | 300 | 560 | 2.5 |
| 6 | 6 | 500 | 0.50 | 2.0 | 12 | 39 | 1.6 | 0.9 | 0 | 2.8 | 280 | 490 | 2.2 |
| 7[2] | 6 | 500 | 0.50 | 1.4 | 17 | 42 | 1.4 | 0 | 1.1 | 2.8 | 280 | 490 | 2.2 |
| 8[3] | 9 | 500 | 0.50 | 9.8 | 2.5 | 39 | 0 | 0 | 0 | 1.9 | 210 | 360 | 2.2 |
| 9 | 9 | 500 | 0.50 | 4.7 | 5.1 | 38 | 1.5 | 1.0 | 0 | 2.2 | 205 | 360 | 2.6 |
| Compar. 5 | B | 450 | 0.07 | 6.6 | 0.5 | 51 | 1.1 | 0.7 | 0 | 2.8 | 230 | 440 | 2.4 |
| Compar. 6[2] | B | 450 | 0.05 | 15 | 0.2 | 56 | 1.0 | 0 | 0.8 | 2.7 | 210 | 400 | 2.5 |
| Compar. 7[3] | C | 450 | 0.30 | 4.41 | 3.3 | 34 | 0 | 0 | 0 | 0.5 | 31 | 220 | 2.9 |
| Compar. 9[3] | D | 450 | 0.30 | 2.90 | 5.0 | 37 | 0 | 0 | 0 | 0.5 | 31 | 250 | 3.1 |
| Compar. 10 | C | 450 | 0.50 | 3.18 | 7.5 | 33 | 2.0 | 1.2 | 0 | 0.5 | 28 | 130 | 4.3 |
| Compar. 11 | D | 450 | 0.50 | 3.48 | 6.9 | 36 | 1.5 | 1.0 | 0 | 0.6 | 44 | 280 | 5.7 |

BHT/Al = 2 mol/mol;
TBF20/Ti = 2 mol/mol;
C3 feed = 400 NL/h;
C2 feed = 200 NL/h;
ENB feed = 0.7 ml;
VNB feed = 0.7 ml;
H2 feed = 0.35 NL/h
T = 90° C.;
P = 7 barg
[1]Calculated value
[2]0.7 ml of DCPD in the feed of the 0.7 ml VNB
[3]Ethylene-propylene copolymerization; no H2 added From the composition of the polymer given in Table 1, it can be concluded that the diene affinity of the catalysts 6 and 9 according to the invention is higher than the diene affinity of the known catalyst B.

RESULTS

Due to the fact that more catalyst leads to more heat formation the used reactor that was optimized to run at 90° C.+/−3° C. the amount of catalyst was chosen to give a heat wherein:
M is a group 4-6 metal;
$R^1$ is a substituent comprising a heteroatom of group 15, and $R^1$ is bonded to the imine carbon atom via the heteroatom;
$R^2$-$R^5$ are the same or different, and each of $R^2$, $R^3$, $R^4$ and $R^5$ represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with at least one optionally substituted C1-20 hydrocarbon group, or a C1-20 hydrocarbon-substituted amino group, and adjacent ones of $R^2$, $R^3$, $R^4$ and $R^5$ may be linked to each other to form a ring;

$R^6$-$R^9$ are the same or different, and each of $R^6$, $R^7$, $R^8$ and $R^9$ represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with at least one optionally substituted C1-20 hydrocarbon group a C1-20 hydrocarbon-substituted amino group and adjacent ones of $R^6$, $R^7$, $R^8$ and $R^9$ may be linked to each other to form a ring;

L is a neutral ligand, and j is an integer denoting the number of neutral ligands L, wherein j is 0 to n, with n being an amount that satisfies 18 electrons of valance shells of the metal M; and X is an anionic ligand, and r is an integer denoting the number of anionic ligands X to provide charge neutrality.

2. The metal complex according to claim 1, wherein M is selected from the group consisting of Ti, Zr and Hf.

3. The metal complex according to claim 1, wherein $R^2$-$R^5$ are the same or different and each represents a hydrogen atom or a C1-5 alkyl group.

4. The metal complex according to claim 1, wherein the heteroatom of group 15 is a nitrogen atom, through which R1 is bonded to the imine carbon atom.

5. The metal complex according to claim 1, wherein X represents a halogen atom, a C1-10 alkyl group, a C7-20 aralkyl group, a C6-20 aryl group, or a C1-20 hydrocarbon-substituted amino group, wherein if r is greater than 1, each X is independently of any other X one of the specified substituents.

6. The metal complex according to claim 1, wherein j is zero.

7. The metal complex according to claim 1, wherein each of $R^6$, $R^7$, $R^8$ and $R^9$ is a hydrogen atom.

8. The metal complex according to claim 1, wherein:
the heteroatom of group 15 is a nitrogen atom, through which R1 is bonded to the imine carbon atom, and $R^1$ is of the general formula —$NR^{10}R^{11}$ with $R^{10}$ and $R^{11}$ being individually selected from the group of aliphatic C1-10 hydrocarbyl, halogenated aliphatic C1-10 hydrocarbyl, aromatic C6-20 hydrocarbyl, and halogenated C6-20 aromatic hydrocarbonyl residues, and $R^{10}$ and $R^{11}$ may be linked to each other to form a ring, or one of $R^{10}$ and $R^{11}$ may be linked with any one of the radicals $R^6$ to $R^9$ to form a ring;
M is selected from the group consisting of Ti, Zr and Hf;
$R^2$-$R^5$ are the same or different and each represents a hydrogen atom or a C1-5 alkyl group;
X represents a halogen atom, a C1-10 alkyl group, a C7-20 aralkyl group, a C6-20 aryl group, or a C1-20 hydrocarbon-substituted amino group, wherein if r is greater than 1, each X is independently of any other X one of the specified substituents;
j is zero; and
each of $R^6$, $R^7$, $R^8$ and $R^9$ is a hydrogen atom.

9. The metal complex according to claim 8, wherein:
$R^1$ is dimethylamide, diisopropylamide, dicyclohexylamide, or N-dimethylphenyl N-ethylamide;
M is Ti;
X is Cl or methyl; and
each of $R^2$, $R^3$, $R^4$ and $R^5$ is methyl.

10. A process for producing the metal complex represented by the formula (I) according to claim 1, the process comprising reacting a substituted cyclopentadiene compound of the formula (2)

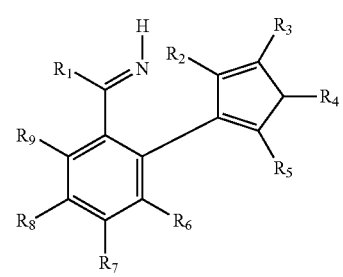

(2)

with a metal compound represented by the formula (3)

$$MX_{(r+2)}L_j \qquad (3).$$

11. A catalyst system comprising:
a) a metal complex of the formula (1) according to claim 1, and
b) an activator.

12. The catalyst system according to claim 11, further comprising a scavenger c), wherein the scavenger c) is a hydrocarbyl of a metal or metalloid of group 1-13, or a reaction product of the hydrocarbyl with at least one sterically hindered compound containing a group 15 or 16 atom.

13. The catalyst system according to claim 11, wherein the activator b) is at least one of a borane, a borate, or an organoaluminum compound.

14. A process for the preparation of a polymer by polymerizing at least one olefinic monomer, the process comprising contacting the monomer with a catalyst system comprising the metal complex according to claim 1.

15. The process according to claim 14, wherein the at least one olefinic monomer comprises ethylene and at least a $C_3$-$C_{12}$-α-olefin.

16. The process according to claim 14, wherein the at least one olefinic monomer comprises ethylene, at least one $C_{3-12}$ alpha olefin, and at least one non-conjugated diene selected from the group consisting of 5-methylene-2-norbornene 5-ethylidene-2-norbornene, 5-vinylnorbornene, 2,5-norbornadiene, dicyclopentadiene and vinylcyclohexane.

17. A compound of the formula (2)

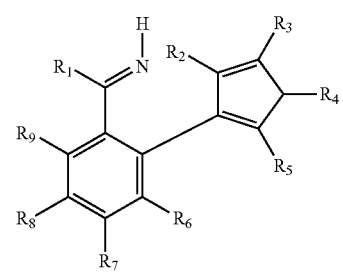

(2)

wherein:
- $R^1$ is a substituent comprising a heteroatom of group 15, and $R^1$ is bonded to the imine carbon atom via the heteroatom;
- $R^2$-$R^5$ are the same or different, and each of $R^2$, $R^3$, $R^4$ and $R^5$ represents a hydrogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with at least one optionally substituted C1-20 hydrocarbon group, or a C1-20 hydrocarbon-substituted amino group, and adjacent ones of $R^2$, $R^3$, $R^4$ and $R^5$ may be linked to each other to form a ring; and
- $R^6$-$R^9$ are the same or different, and each of $R^6$, $R^7$, $R^8$ and $R^9$ represents a hydrogen atom, a halogen atom, an optionally substituted C1-10 alkyl group, an optionally substituted C1-10 alkoxy group, an optionally substituted C6-20 aryl group, an optionally substituted C6-20 aryloxy group, an optionally substituted C7-20 aralkyl group, an optionally substituted C7-20 aralkyloxy group, a silyl group substituted with at least one optionally substituted C1-20 hydrocarbon group, a C1-20 hydrocarbon-substituted amino group and adjacent ones of $R^6$, $R^7$, $R^8$ and $R^9$ may be linked to each other to form a ring.

18. A process for the manufacturing of a compound of the formula (2) according to claim 17, the process comprising reacting at least one of a nitrile of formula (4) and an oxime of formula (5)

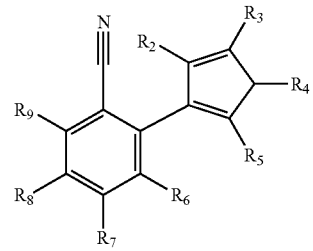

(4)

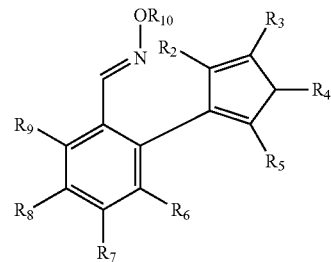

(5)

with at least one of an organic lithium compound $LiR^1$ and an organic magnesium compound $Mg(Hal)R^1$ wherein
- $R^{10}$ represents a hydrogen atom, an optionally substituted C1-10 alkyl group, an optionally substituted C6-20 aryl group, an optionally substituted C7-20 aralkyl group, or a silyl group optionally substituted with at least one optionally substituted C1-20 hydrocarbon, and
- Hal means a halide.

* * * * *